United States Patent
Ala et al.

(10) Patent No.: US 7,345,048 B2
(45) Date of Patent: Mar. 18, 2008

(54) HETEROCYCLIC COMPOUNDS AND USES THEREOF AS D-ALANYL-D-ALANINE LIGASE INHIBITORS

(75) Inventors: Paul J. Ala, Newark, DE (US); Janid A. Ali, Waltham, MA (US); Jacob J. Clement, Vancouver (CA); Patrick R. Connelly, Harvard, MA (US); Carlos H. Faerman, Acton, MA (US); Christopher Faraday, San Francisco, CA (US); John V. Gazzaniga, Worcester, MA (US); Andrew S. Magee, Maynard, MA (US); Salvatore A. Marchese, Malden, MA (US); Scott T. Moe, Marlborough, MA (US); Manuel A. Navia, Lexington, MA (US); Emanuele Perola, Cambridge, MA (US); Paul Will, Stoneham, MA (US)

(73) Assignee: Pliva D.D., Zagreb (HR)

( * ) Notice: Subject to any disclaimer, the term of this patent is extended or adjusted under 35 U.S.C. 154(b) by 0 days.

(21) Appl. No.: 10/185,059

(22) Filed: Jun. 28, 2002

(65) Prior Publication Data

US 2003/0181470 A1 Sep. 25, 2003

Related U.S. Application Data

(60) Provisional application No. 60/301,685, filed on Jun. 28, 2001.

(51) Int. Cl.
| | | |
|---|---|---|
| C07D 487/94 | (2006.01) | |
| C07D 475/08 | (2006.01) | |
| C07D 239/48 | (2006.01) | |
| A61K 31/519 | (2006.01) | |
| A61P 31/04 | (2006.01) | |

(52) U.S. Cl. ............ 514/262.1; 544/256; 544/323; 544/324; 560/28; 564/336

(58) Field of Classification Search ............ None
See application file for complete search history.

(56) References Cited

U.S. PATENT DOCUMENTS

| 2,949,466 | A | * | 8/1960 | Hoefle et al. ............... 544/256 |
| 4,256,738 | A | * | 3/1981 | Woitun et al. ............... 514/29 |
| 5,593,998 | A | | 1/1997 | Henrie et al. |

FOREIGN PATENT DOCUMENTS

| EP | 185 259 A2 | 5/1985 |
| JP | 2000-239277 | 9/2000 |
| RO | 56210 | 4/1974 |
| WO | WO 92/17478 | 10/1992 |
| WO | WO 99/50264 | 10/1999 |
| WO | WO 2004/020417 | 3/2004 |

OTHER PUBLICATIONS

Weinstock, J. Med. Chem 11(3), 1968, pp. 573-579.*
Wang, Heterocycles 48(9) 1923 (1998).*
Taylor, JACS 82, 5711 (1960).*
Gangjee et al., Bioorg Med Chem., Nov. 2001, 9(11):2929-2935, (abstract only).
Smith et al., Clinical Cancer Research, Jul. 2001, 7:2105-2113.
Borhani et al., Experimental Progress Reports, 1997, 7-105 to 7-107.
Wang, Heterocycles 48, 1923 (1998).
Weinstock, J Med Chem 11(3) 573 (1968).
Pettit, et al., J. Carbohydrates, Nucleosides, Nucleotides, 7(5):315-332 (1980).
Hurlbert et al., J Med Chem, 11(4):711-717 (Jul. 1968).
Elslager et al., J Med Chem, 24(2):127-40 (Feb. 1981).
Chemical Abstracts 133:296425, (index entry for compound).
Chemical Abstracts 133:193165, (index entry for compound).

* cited by examiner

Primary Examiner—Mark L. Berch
(74) Attorney, Agent, or Firm—Darby & Darby P.C.

(57) ABSTRACT

The invention relates to D-Ala-D-Ala ligase inhibitors having the formula:

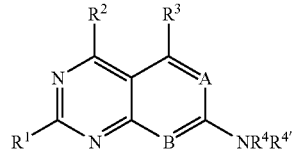

wherein $R^1$ is $NH_2$; $R^2$ is $NH_2$; $R^3$ is selected from hydrogen, alkyl, amino, hydroxy, alkoxy, and alkylamino; and $R^4$ and $R^{4'}$ are each independently hydrogen or a substituted or unsubstituted, linear, branched, or cyclic, alkyl, alkenyl, alkynyl, aryl, acyl, aralkyl, or alkaryl group wherein one or more carbon or hydrogen atoms may be substituted by a substituent selected from amino, alkylamino, hydroxyl, alkoxyl, thio, halogen, nitro, and carbonyl; wherein $NR^4R^{4'}$ incorporates a substituted or unsubstituted naphthyl group, wherein the substituents are selected from alkoxy, halogen, alkyl, and alkylene, and wherein said naphthyl group in $NR^4R^{4'}$ is bonded to N through a substituted or unsubstituted alkylene moiety. These compounds have antibacterial properties based on their ability to bind and inhibit D-Ala-D-Ala ligase, a critical pathway enzyme in bacterial cell-wall synthesis, and are suitable for various antibacterial uses.

22 Claims, No Drawings

HETEROCYCLIC COMPOUNDS AND USES THEREOF AS D-ALANYL-D-ALANINE LIGASE INHIBITORS

CROSS-REFERENCE TO RELATED APPLICATION

This application claims the benefit of U.S. Provisional Application No. 60/301,685, filed Jun. 28, 2001, which is hereby incorporated by reference in its entirety.

FIELD OF THE INVENTION

This invention relates to heterocyclic compounds and to their use, for example, in the prophylaxis and or medical treatment of bacterial infections and their use, for example, as antiseptics, sterilizants, or disinfectants.

BACKGROUND OF THE INVENTION

The pathogenic processes by which microorganisms elicit their adverse effects on subjects are generally complex and require a defined sequence of events that implicate multiple microbial components. If left unchecked, the proliferation of organisms can impair the subject, resulting in chronic infection, or even death. It is frequently necessary to bolster host defense mechanisms with exogenous factors such as antibiotics to aid clearance of the infecting organism from the subject.

Over time, and due in part to injudicious use of existing antibiotic treatment regimens, organisms are becoming increasingly resistant to the various exogenous factors available. For example, resistance of bacteria to fluoroquinolones and beta-lactams has been reported and will most probably increase over the next decade. Fluoroquinolone resistance isolates from around of the world in community-acquired pneumonia have also been increasingly described. Further, there is a serious decrease in susceptibility of *E. coli* strains to the beta-lactams (e.g., amoxicillin), due to the presence of R-TEM enzymes, to cotrimoxazole and trimethoprim. These reports exemplify the necessity and continued need for the discovery and development of new antimicrobial therapeutics in order to provide alternative and more powerful treatment regimens against increasingly resistant microorganisms.

SUMMARY OF THE INVENTION

The invention relates to heterocyclic compounds, compositions comprising the compounds, and methods of using the compounds and compound compositions. The compounds and compositions comprising them are useful for treating disease or disease symptoms. The invention also provides for methods of making the compounds and methods for identifying compounds with desired biological activity.

The invention is based on the discovery that certain heterocyclic compounds have potent antibacterial activity, and more specifically, activity against the enzyme D-alanyl-D-alanine ligase ("D-Ala-D-Ala ligase"; E.C. 6.3.2.4). As shown in the schematic below, D-Ala-D-Ala ligase is believed to play a critical role in bacterial cell growth by catalyzing assembly of D-alanyl-D-alanine ("D-Ala-D-Ala"), one of the building blocks used for peptidoglycan crosslinking essential for bacterial cell wall biosynthesis. It is thought that the enzyme establishes a peptide linkage that ultimately provides the site of transacylation when the peptidoglycan framework is crosslinked (Ellsworth et al., *Chemistry & Biology*, 3:37-44, 1996). Without intending to be bound by any theory as to the mechanism of action of the new compounds, the new compounds are believed to bind to the adenosine triphosphate- (ATP-) binding site of D-Ala-D-Ala ligase, and not to the D-Ala-binding site, making the compounds competitive versus ATP. The compounds therefore differ in this regard from other D-Ala-D-Ala ligase inhibitors such as cycloserine and dipeptide phosphonate analogs, which are competitive inhibitors for D-alanine and are believed to bind to the D-alanine-binding site of the enzyme.

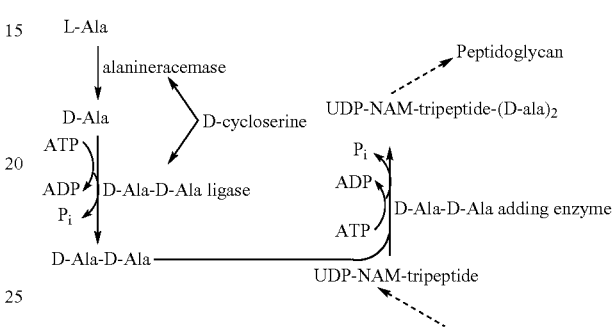

In general, the invention features compounds of the following general structures:

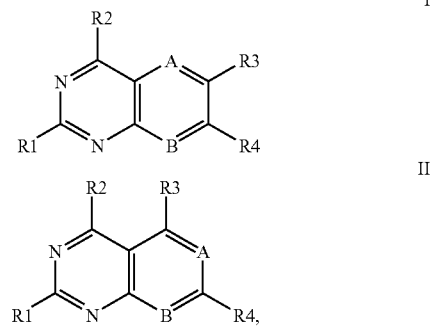

and uses thereof.

In particular, in one embodiment, the invention features a compound having the formula:

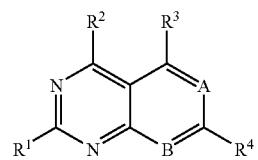

where A and B can independently be either N or $CR^7$, where $R^7$ is hydrogen or a carbon-, nitrogen-, sulfur-halogen- and/or oxygen-containing function group (e.g., hydrogen, or a substituted or unsubstituted, linear, branched, or cyclic, alkyl, alkenyl, alkynyl, aryl, aralkyl, or alkaryl group, or a derivative of one or more of these groups where heteroatoms are substituted for one or more of the carbon and/or hydrogen atoms (e.g., amino groups, alkylamino groups, hydroxyl and alkoxyl groups, thiol groups, halogens, nitro groups, phenolic groups, or other substituted aromatic or aliphatic groups)). $R^1$ and $R^2$ are identical or different —$NR^5R^6$ groups, where each $R^5$ and $R^6$ can independently be hydrogen or a carbon-containing functional group. $R^3$ is hydrogen or an alkyl, amino, hydroxy, alkoxy, or alkylamino group. $R^4$ is a carbon-, nitrogen-, sulfur-, halogen-, and/or oxygen-containing functional group, provided that, (1) if A and B are both nitrogen and $R^5$ and $R^6$ are both hydrogen, then $R^4$ is not —$NH_2$, —$N(H)(methyl)$, —$N(H)(butyl)$, —$N(H)(hexyl)$, —$N(H)(phenyl)$, —$N(H)(benzyl)$, —$N(H)(NH_2)$, —$N(H)(CH_2CH_2OH)$, —$N(CH_2CH_2OH)_2$, phenyl, N-piperadinyl, or —$S(ethyl)$;

(2) if A is CH, B is nitrogen, and $R^5$ and $R^6$ are both hydrogen, then $R^4$ is not methyl, isobutyl, phenyl, 4-methylphenyl, 4-chlorophenyl, 4-bromophenyl, 2-(2,5-dimethoxyphenyl)-ethyl, or —$CH(OCH_3)_2$; and (3) if A and B are both CH groups, then $R^4$ is an amino group other than —$NH_2$, (3,4-dichlorophenyl)methylamino, or (3,4-dichlorophenyl)methyleneimino.

In some cases $R^5$ and $R^6$ are both hydrogen.

$R^4$ can be, for example, a substituted or unsubstituted, linear, branched, or cyclic, alkyl, alkenyl, alkynyl, aryl, aralkyl, or alkaryl group. In some cases, $R^4$ includes at least one aryl group. For example, $R^4$ can be one of the following groups:

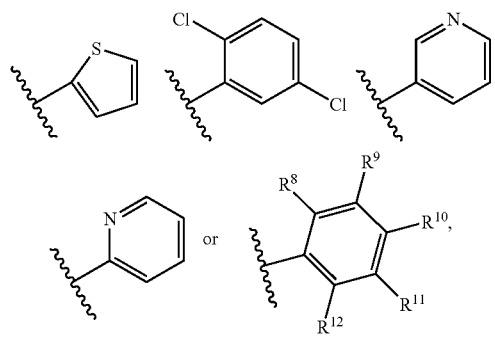

where $R^{8-12}$ can independently be hydrogen or a carbon-, nitrogen-, sulfur-halogen- and/or oxygen-containing functional group (e.g., a linear or branched alkyl).

In another example where $R^4$ includes an aryl group, the compound has the structure:

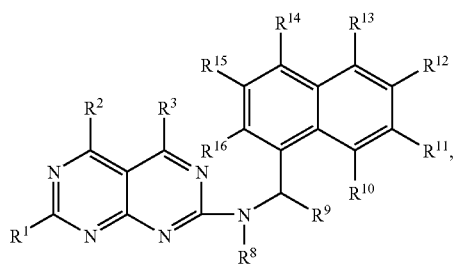

where $R^{8-16}$ can independently be hydrogen or a carbon-, nitrogen-, sulfur-halogen- and/or oxygen-containing functional groups. For example, $R^9$ can be hydrogen or methyl. In some cases, the compound has the structure:

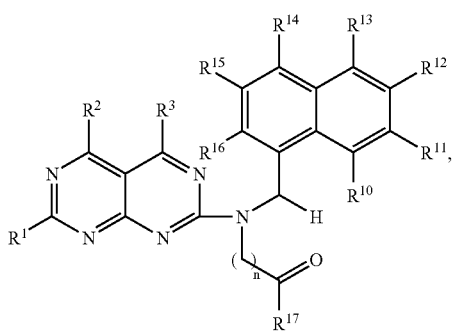

where n is 1, 2, 3, or 4; and $R^1$ is —$NR^{18}R^{19}$, where $R^{18}$ and $R^{19}$ can independently be hydrogen or a carbon-, nitrogen-, sulfur-halogen- and/or oxygen-containing functional group. In some cases, for example, $R^{17}$ can be one of the following moieties:

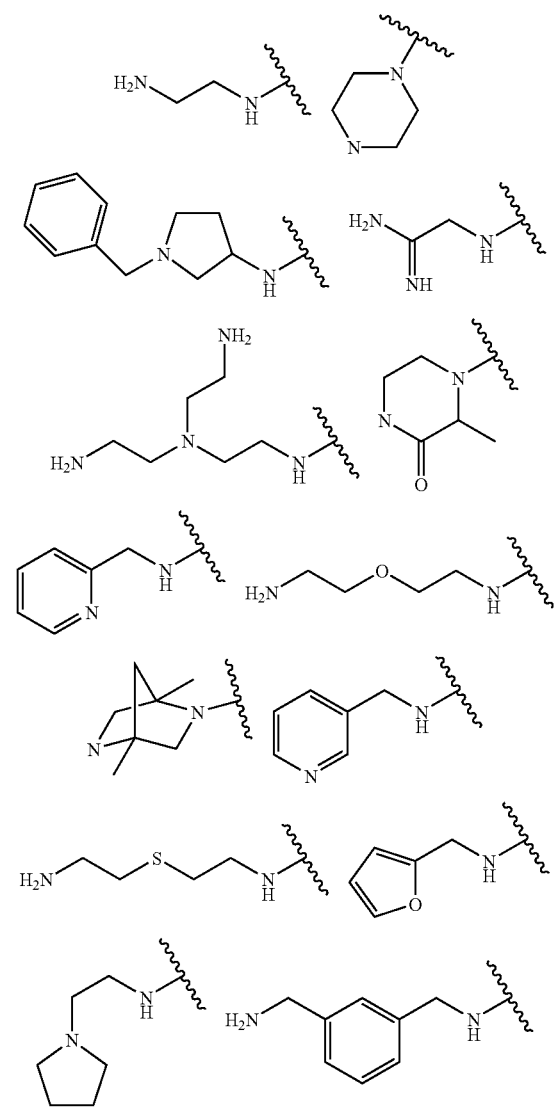

-continued

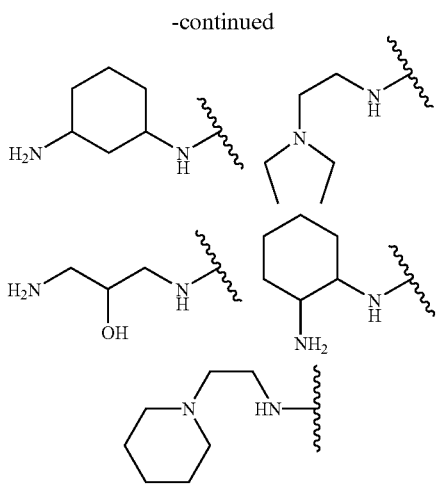

R⁸ can alternatively be, for example, —(CH₂)ₙNR¹⁸R¹⁹, where n is 1, 2, 3, or 4; and R¹⁸ and R¹⁹ can independently be hydrogen or a carbon-, nitrogen-, sulfur-halogen- and/or oxygen-containing functional group.

R⁴ can, alternatively, be —CH₂O-aryl, —CH₂S-aryl, —CH=CH-aryl, or —NH(CH₂-aryl), where the aryl group can be any aromatic moiety, whether comprising carbon and hydrogen only (e.g., phenyl, naphthyl, toluyl) or including other atoms (e.g., pyrrolyl, pyridyl, oxazolyl, chlorophenyl, bromonaphthyl).

R⁴ can, alternatively, be —N(CH₃)R²¹, —N(CH₂CH₃)R²¹, —N(CH(CH₃)₂)R²¹, —N(benzyl)R²¹, —CH₂NH₂, —NHCH₂CH₂NR²²R²³, or —CH₂NHC(=O)R²², wherein R²¹⁻²³ can independently be hydrogen or a carbon-, nitrogen-, sulfur-halogen- and/or oxygen-containing functional group. In specific cases, R²² is hydrogen and R²³ is —C(=O)R²⁴, where R²⁴ is hydrogen or a carbon-, nitrogen-, sulfur-halogen- and/or oxygen-containing functional group.

In still other cases, R⁴ can be such that the compound has the following structure:

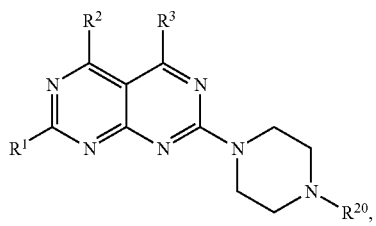

where R²⁰ is hydrogen or a carbon-, nitrogen-, sulfur-halogen- and/or oxygen-containing functional group.

In other cases, R⁴ can be such that the compound has the structure:

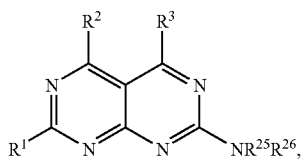

where R²⁵ and R²⁶ can independently be hydrogen or a carbon-, nitrogen-, sulfur-halogen- and/or oxygen-containing functional group. For example, R²⁵ can be hydrogen, alkyl, hydroxyalkyl, or aralkyl, and R²⁶ can be haloalkyl, hydroxyl, C(=O)NR²⁷R²⁸, C(=O)OR²⁷, or NR²⁷R²⁸, where R²⁷ and R²⁸ can independently be hydrogen or a carbon-, nitrogen-, sulfur-halogen- and/or oxygen-containing functional group. R²⁶ can alternatively be —C(H)(aryl)(R²⁹), where R²⁹ is hydrogen or a carbon-, nitrogen-, sulfur-halogen- and/or oxygen-containing functional group. In some cases, R²⁹ includes at least one acyl group (e.g., a carboxylate, ketone, aldehyde, ester, amide, or thioester group). In these or other cases, the aryl group can be a naphthyl or benzothiophenyl group. R²⁹ can include an alpha-hydroxy carboxylate group (e.g., a —C(R)(OH)(COOR') group, where R and R' can be hydrogen or a carbon-, nitrogen-, sulfur-halogen- and/or oxygen-containing functional group).

In another embodiment, the invention features a compound having the formula:

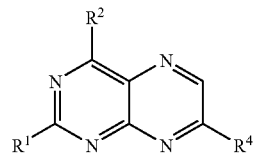

where R¹ and R² are identical or different —NR⁵R⁶ groups, where each R⁵ and R⁶ can independently be hydrogen or a carbon-containing functional group; and R⁴ is an amino group other than —NH₂ or

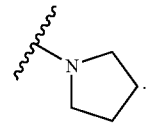

In still another embodiment, the invention features a method of inhibiting D-alanyl-D-alanine (D-Ala-D-Ala) ligase. The method includes the step of exposing D-Ala-D-Ala ligase to a compound of formula I or formula II:

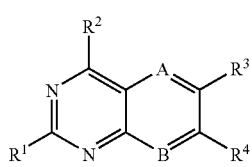

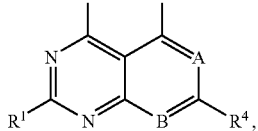

where
A and B can independently be N or CR⁷, where R⁷ is hydrogen or a carbon-, nitrogen-, sulfur-halogen- and/or oxygen-containing function group; R¹ and R² are identical or different —NR⁵R⁶ groups, where each R⁵ and R⁶ can independently be hydrogen or a carbon-containing functional group; R³ and R⁴ can independently be hydrogen or a carbon-, nitrogen-, sulfur-, halogen-, and/or oxygen-containing functional group; provided that R³ and R⁴ are not both hydrogen.

For example, R¹ and R² can both be —NH₂.

In some cases, R³ and R⁴ can independently be -branched or straight-chain alkyl, —O-alkyl, —O-alkyl-COOH, —O-alkyl-NR⁷R⁸, —O-alkyl-OH, —NR⁷R⁸, —NR⁷-alkyl-NR⁸R⁹, —NR⁷-alkyl-COOH, —NR⁷-alkyl-OH; —CONR⁷R⁸, —CONR⁷-alkyl-NR⁸R⁹, —CONR⁷-alkyl-COOH, —CONR⁷-alkyl-OH, —S-alkyl, —S-alkyl-COOH, —S-alkyl-NR⁷R⁸, —S-alkyl-OH, —O-aryl, —O-aryl-COOH, —O-aryl-NR⁷R⁸, —O-aryl-OH, —S-aryl, —S-aryl-COOH, —S-aryl-NR⁷R⁸, —S-aryl-OH, —NR⁷-aryl-NR⁸R⁹, —NR⁷-aryl-COOH, —NR⁷-aryl-OH; —CONR⁷-aryl-NR⁸R⁹, —CONR⁷-aryl-COOH, —CONR⁷-aryl-OH, or —CH₂NR⁵C₆H₄COOH; provided that R³ and R⁴ cannot simultaneously be identical branched or straight chain alkyl groups; R¹ and R² can independently be hydrogen, —NH₂, or —NR¹¹R¹², where at least one of R¹ and R² is —NH₂; R⁵ can be lower alkyl (i.e., C₁₋₆ alkyl), hydrogen, or —CH₂NR¹⁰C₆H₄CONHR⁶; where R⁶ is -alkyl, -alkyl-COOH, -alkyl-NH₂, or -alkyl-OH; R⁷, R⁸, R⁹, R¹⁰, R¹¹, and R¹² can independently be straight-chain alkyl, branched alkyl, aryl, or acyl groups, optionally substituted with one or more oxygen, nitrogen, sulfur, or halogen-based functional groups; and A can be N and CH.

The D-Ala-D-Ala ligase inhibited can, for example, include a sequence at least 90% identical to the sequence of a D-Ala-D-Ala ligase from a species selected, for example, from the group consisting of *Escherichia coli, Chlamydophila pneumoniae, Chlamydia trachomatis, Yersinia pestis, Haemophilus influenzae, Haemophilus ducreyi, Pseudomonas aeruginosa, Pseudomonas putida, Xylella fastidiosa, Bordetella pertussis, Thiobacillus ferrooxidans, Neisseria meningitidis, Neisseria gonorrhoeae, Buchnera aphidicola, Bacillus halodurans, Geobacter sulfurreducens, Rickettsia prowazekii, Zymomonas mobilis, Aquifex aeolicus thermophile, Thermotoga maritima, Clostridium difficile, Enterococcus faecium, Streptomyces toyocaensis, Amycolatopsis orientalis, Enterococcus gallinarum, Enterococcus hirae, Enterococcus faecium, Enterococcus faecalis, Streptococcus pneumoniae, Streptococcus pyogenes, Staphylococcus aureus, Bacillus subtilis, Bacillus stearothermophilus, Deinococcus radiodurans, Synechocystis sp., Salmonella typhimurium, Mycobacterium tuberculosis, Mycobacterium avium, Mycobacterium smegmatis, Legionella pneumophila, Leuconostoc mesenteroides, Borrelia burgdorferi, Treponema pallidum, Vibrio cholerae,* and *Helicobacter pylori.*

In yet another embodiment, the invention features a method of treating a patient. The method includes the step of administering to the patient an effective amount of a compound of formula I or formula II:

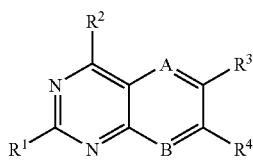

I

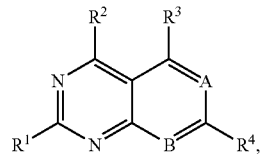

II where A, B, and R¹⁻⁴ are defined as above.

The invention also features a formulation that includes any of the above compounds combined with an excipient suitable for administration to a subject.

The invention also features a method of treating a subject having a bacterial microbial infection. The method includes administering to the subject an effective amount of a formulation as described above. The subject can be, for example, an animal such as a mammal (for example, a human, a horse, a lamb, a dog, a cat, a rabbit, a mouse, a rat, a cow, a bull, a pig), a bird (for example, a chicken, a goose, a turkey, a duck, a fowl), a fish (for example, a salmon, a trout, a catfish, a goldfish), or other farm, companion, or ornamental animal.

In yet another embodiment, the invention features a method of treating a patient. The method includes the step of administering to the patient an effective amount of any of the above compounds, optionally with a suitable carrier.

In still another embodiment, the invention features a method of inhibiting bacteria growth in a non-living system (e.g., sterilizing, disinfecting, killing bacteria in vitro). The method includes the step of contacting the system (e.g., a medium, a medical device, a kitchen or bathroom surface, an operating theater), with an effective amount of any of the above compounds, to inhibit bacterial growth.

Several parameters can be used in the selection of compounds for use in the new methods. The parameters include, but are not limited to, in vitro antibacterial potency and spectrum of activity; physical-chemical properties such as lipophilicity and solubility. The pharmacokinetic performance of the compounds of the invention, as well as their in vitro antibacterial activity, indicates that the compounds of the invention are useful both in the prophylaxis and medical treatment of subjects that have bacterial infections and as antiseptics, sterilizants, or disinfectants.

The terms "halo" and "halogen" refer to any radical of fluorine, chlorine, bromine or iodine.

The terms "alkyl", "alkenyl" and "alkynyl" refer to hydrocarbon chains that may be straight-chain or branched-chain, containing the indicated number of carbon atoms, if specified. For example, "C₁₋₁₀" or "C1-C10" indicates the group may have from 1 to 10 (inclusive) carbon atoms in it, or may by cyclic (e.g., including one or more rings). The terms "ring" and "ring system" refer to a ring comprising the delineated number of atoms, said atoms being carbon or, where indicated, a heteroatom such as nitrogen, oxygen or sulfur (e.g., including a heterocyclyl group). The ring itself, as well as any substituents thereon, may be attached at any atom that allows a stable compound to be formed.

The term "aryl" refers to a 6-carbon monocyclic or 10-carbon bicyclic aromatic ring system wherein 0, 1, 2 or 3 atoms of each ring may be substituted by a substituent. Examples of aryl groups include phenyl, naphthyl and the like, as well as heteroaryl groups.

The term "heteroaryl" refers to an aromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2 or 3 atoms of each ring may be substituted by a substituent. Examples of heteroaryl groups include pyridyl, faryl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2 or 3 atoms of each ring may be substituted by a substituent. Examples of heterocyclyl groups include piperizinyl, pyrrolidinyl, dioxanyl, morpholinyl, tetrahydrofuranyl, and the like.

Combinations of substituents and variables envisioned by this invention are only those that result in the formation of stable compounds. The term "stable", as used herein, refers to compounds that possess stability sufficient to allow manufacture and that maintains the integrity of the compound for a sufficient period of time to be useful for the purposes detailed herein (e.g., therapeutic or prophylactic administration to a subject or patient, or antiseptic, wound dressing impregnation, sterilizant, or disinfectant applications).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

The invention can provide several advantages over the existing methods of treatment. For example, the compounds of the invention can bind to the ATP-binding site of the D-Ala-D-Ala ligase enzyme with high specificity and are shown to be competitive with ATP in biochemical assays. Some compounds described in this invention have their protein-interacting functional groups situated so as to be able to also bind to one or both of the D-alanine binding sites of D-Ala-D-Ala ligase. These types of new compounds (bisubstrate analogs) may have further enhanced selectivity and potency directly associated with the ability to bridge the ATP site and D-Ala site.

Some of the compounds of the invention may also be less toxic than many existing antibiotics. The new compounds bind specifically to D-Ala-D-Ala ligase, an enzyme found in bacteria but not in human or other eukaryotic cells, so the new compounds generally do not interfere with biological systems in patients. Since peptidoglycans are present only in bacteria, and are absent from mammalian cells, specific inhibition of D-Ala-D-Ala ligase can result in highly selective antibacterial activity.

Moreover, some compounds of the invention may have several chemical and pharmacological advantages over existing compounds used in treating bacterial infections. These advantages may include both chemical stability and pharmacological stability, as well as potency, different resistance profiles, different selectivity profiles, and decreased side-effects. The new compounds' activity and ability to cross bacterial cell membranes also makes them suitable for use as antibiotic drugs. The invention also envisions veterinary uses for the treatment of infections in fish, fowl, livestock, other food animals, sports animals, and companion animals.

The compounds of the invention have displayed potent broad spectrum activity against a representative panel of microorganisms, including *E. coli S. aureus, S. pneumoniae, H. influenzae*, and others. Broad spectrum activity is also inferred from the close sequence homology in the D-Ala-D-Ala ligases of fifty-one representative, but evolutionarily diverse, microorganisms representative of all bacteria. Nonetheless, individual compounds do have greater activity against specific bacteria, creating opportunities for the development of selective and specific narrow-spectrum agents as well.

Other features and advantages of the invention will be apparent from the following detailed description, and from the claims.

DETAILED DESCRIPTION OF THE INVENTION

The invention relates to the specific compounds exemplified herein. Thus one embodiment of the invention is any compound specifically delineated herein, including the compounds listed below:

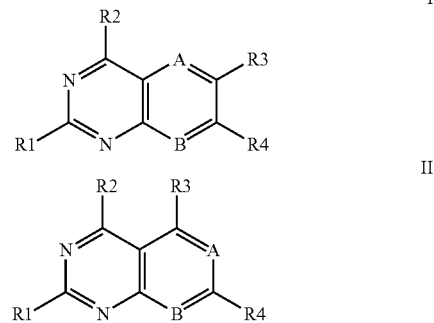

where A and B of structures I or II is independently either —N—, —CH—, or —CR$^7$—. $R^1$, $R^2$, $R^3$, $R^4$, and $R^7$ are independently selected.

The compounds of this invention can be synthesized using conventional techniques. Advantageously, these compounds are conveniently synthesized from readily available starting materials. In general, the compounds of the formulae described herein are conveniently obtained via methods illustrated in the schemes and the Examples herein.

Thus, one embodiment relates to a method of making a compound of the formulae described herein, comprising synthesizing any one or more intermediates illustrated in the synthetic schemes herein and then converting that intermediate(s) to a compound of the formulae described herein. Another embodiment relates to a method of making a compound of the formulae described herein, comprising synthesizing any one or more intermediates illustrated in the examples herein and then converting that intermediate(s) to a compound of the formulae described herein. Another embodiment relates to a method of making a compound of the formulae described herein, comprising synthesizing any one or more intermediates illustrated in the synthetic schemes herein and then converting that intermediate(s) to a compound of the formulae described herein utilizing one or more of the chemical reactions described in the synthetic schemes or examples herein. Nucleophilic agents are known in the art and are described in the chemical texts and treatises referred to herein. The chemicals used in the aforementioned methods can include, for example, solvents, reagents, catalysts, protecting group and deprotecting group reagents, and the like. The methods described above can also additionally comprise steps, either before or after the steps described specifically herein, to add or remove suitable protecting groups to ultimately allow synthesis of the compound of the formulae described herein.

As can be appreciated by the skilled artisan, the synthetic schemes herein are not intended to comprise a comprehensive list of all means by which the compounds described and claimed in this application can be synthesized. Additionally, the various synthetic steps described above can be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); M. B. Smith and J. March, *March's Advanced Organic Chemistry: Reactions, Mechanisms, and Structure*, 5th Ed., Wiley Interscience (2001); and L. Paquette, ed., *Encyclopedia of Reagents for Organic Synthesis*, John Wiley and Sons (1995), and subsequent editions thereof.

In a typical method, compounds can be screened for antibacterial activity against a plurality of different bacterial strains. Compounds are assayed for potency and breadth of activity against several strains in order to identify potential lead compounds. The compounds can be screened for bacteriostatic activity (i.e., prevention of bacterial growth) and/or bacteriocidal activity (i.e., killing of bacteria). The lead compounds can be optimized, for example, by varying substituents to produce derivative compounds. The derivatives can be produced one at a time or can be prepared using parallel or combinatorial synthetic methods. In either case, the derivatives can be assayed to generate structure-activity relationship (SAR) data, which can then be used to further optimize the leads.

Design, Synthesis, and Biochemical Evaluation of Ligase Inhibitors

Analogs were designed using a variety of approaches including, traditional medicinal chemistry, systematic analoging (e.g., systematically testing analogs with varying alkyl chain lengths, isosteric functional groups, various aromatic substituents), residue targeting using X-ray crystal structure analysis, molecular modeling and computer active-site docking experiments, computational diversity analysis, and iterative feedback using the results from biochemical experiments. The analogs were synthesized using a variety of synthetic methodologies previously described in the literature by skilled artisans of the craft. The rendered analogs were then analyzed using the described biochemical methods herein to generate potency data. A diverse sample of some of the analogs is described below.

We have identified a variety of substituents on the 6 and 7 positions of quinazolines, pteridines, pyridopyrimidines and pyrimidinopyrimdines that have potent ligase inhibitory activity. Table 1 below shows the diversity of substituents on the 6 and 7 positions capable of inhibiting the ligase enzyme (hydrogen atoms necessary to complete the valence of nitrogen, oxygen, and carbon atoms in the compounds are not shown, but would be understood to be present by one of ordinary skill in the art).

TABLE 1

| Structure | Ki (*E. coli* ligase)/ μM |
|---|---|
| 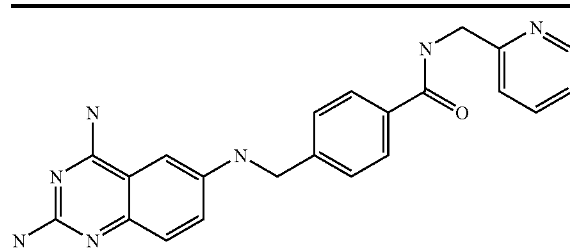 | 73 |
| 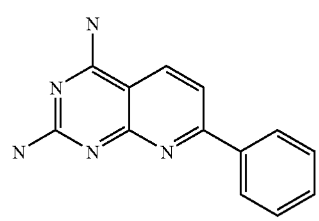 | 31 |
| 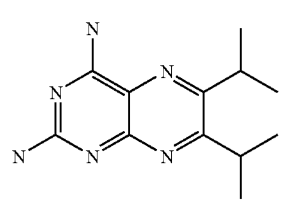 | 37 |

TABLE 1-continued
| Structure | Ki (*E. coli* ligase)/ μM |
|---|---|
| 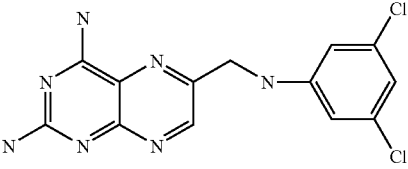 | 1 |
| 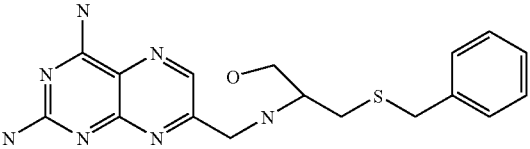 | 55 |
| 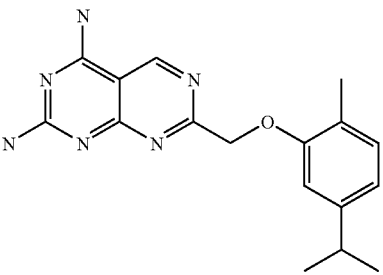 | 20 |
| 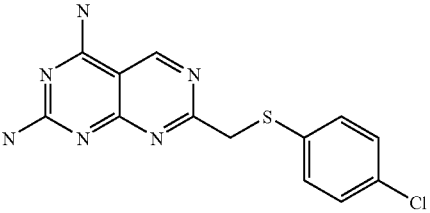 | 12 |
| 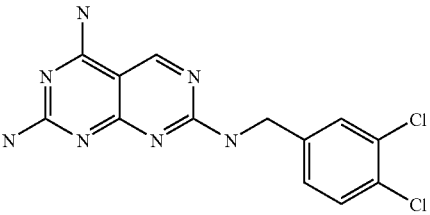 | 20 |
| 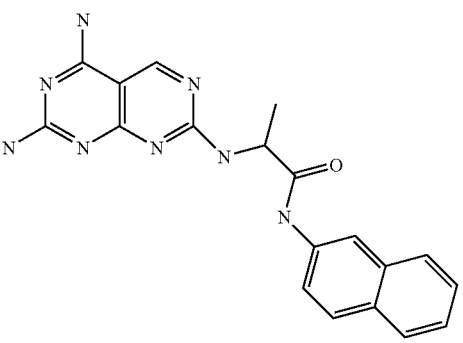 | 29 |

TABLE 1-continued

| Structure | Ki (*E. coli* ligase)/ μM |
|---|---|
| [pteridine with styryl substituent] | 14 |
| [pteridine with (1S)-tetrahydronaphthyl-amino substituent, Chiral] | 16 |
| [pteridine with N-methyl-N-(naphthalen-1-ylmethyl)amino substituent] | 3 |
| [pteridine with N-methyl-N-[3-(dibenzosuberylidene)propyl]amino substituent] | 9 |
| [pteridine with (3S)-1-benzylpyrrolidin-3-ylamino substituent] | 13 |
| [pteridine with 3-(4-chlorophenyl)-3,8-diazabicyclo substituent] | 12 |

TABLE 1-continued

| Structure | Ki (*E. coli* ligase)/ μM |
|---|---|
| (structure) | 2 |
| (structure) | 12 |
| (structure) | 92 |
| (structure) | 14 |
| (structure) | 0.59 |
| (structure) | 0.50 |

TABLE 1-continued
| Structure | Ki (*E. coli* ligase)/ μM |
|---|---|
| 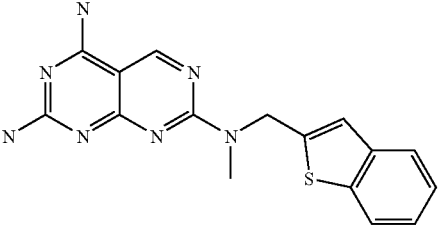 | 2.9 |
| 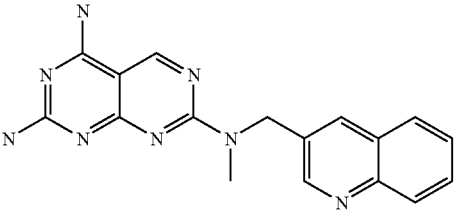 | 1.00 |
| 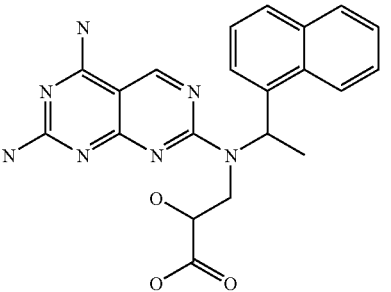 | 0.50 |
| 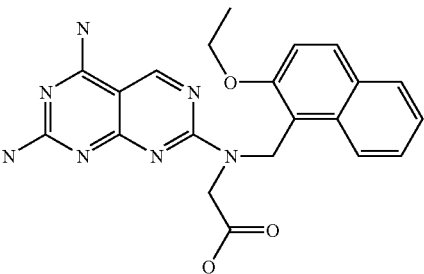 | 8.7 |
| 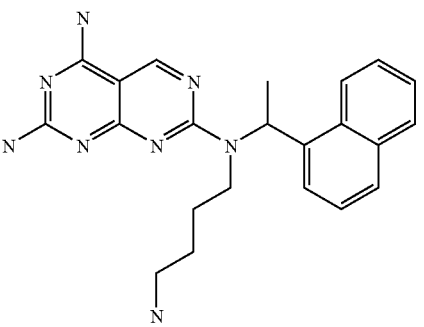 | 0.13 |

N7-Substitution Using Lower Alkyl Groups

Various analogs of the N7-nitrogen (R1 in Table 2 below) can be made to increase potency. Methyl, ethyl, allyl, and cyclopropyl methyl were the most potent lower alkyl and cycloalkyl substitutents identified. Substitution at the alpha-position (R2 in Table 2) was allowed, in some cases $CH_3$ and $C_2H_5$ dramatically improved activity. It would not be surprising if other substituents at the R2 position would increase the potency of ligase inhibition as well. Substitution of the naphthyl ring in the 4-position increased potency using —H, —$CH_3$, or -halogen. Replacement of the naphthyl ring with various hetero cycles (for example, benzothiophene) was found to yield analogs having potent in vitro enzymatic activity. In this series of analogs, the R-alpha-methyl stereoisomers were significantly more potent than the racemates. The S-alpha-methyl stereoconfiguration provided analogs with broader spectrum ligase potency, at the cost of high intrinsic activity against the *E. coli* ligase.

TABLE 2

| N-R1 | R2 | R2 chirality | R3 | E. coli ligase (μM) | Staph ligase (μM) |
|---|---|---|---|---|---|
| —CH3 | CH3 | R/S | H | 0.718 | 9.28 |
| —CH3 | C2H5 | R/S | H | 0.452 | 4.60 |
| —CH3 | CH3 | R | H | 0.326 | 26.80 |
| —CH3 | CH3 | R/S | CH3 | 0.277 | 12.25 |
| —CH3 | CH3 | R/S | 4,5-butylene | 0.240 | 12.00 |
| —CH3 | CH3 | R/S | Cl | 0.201 | 4.90 |
| CH3 | CH3 | R | F | 0.104 | 27.00 |

TABLE 2-continued

| N-R1 | R2 | R2 chirality | R3 | E. coli ligase (μM) | Staph ligase (μM) |
|---|---|---|---|---|---|
| —CH2CH3 | CH3 | R/S | F | 0.257 | 19.00 |
| —CH2CH3 | CH3 | R/S | CH3 | 0.210 | 38.50 |
| —CH2CH3 | CH3 | R | CH3 | 0.102 | 71.00 |
| —CH2CH=CH2 | CH3 | R/S | H | 0.258 | 30.50 |
| —CH2CH(CH2)2 | CH3 | R/S | H | 0.345 | 17.00 |
| —CH2CH(CH2)2 | CH3 | R/S | Br | 0.279 | 25.00 |
| —CH2CH(CH2)2 | CH3 | R/S | CH3 | 0.211 | 37.00 |
| —CH2CH(CH2)2 | CH3 | R/S | Cl | 0.179 | 29.00 |
| —CH2CH(CH2)2 | CH3 | R | CH3 | 0.174 | 62.00 |

Beta-alanine Amides Analogs

Amides synthesized using the beta-alanine linker had broad-spectrum activity. The most potent, broad-spectrum inhibitor identified from this series was an ethylenediamine amide derivative (i.e., the first compound in Table 3 below), which had Ki's for *E. coli* and *H. influenzae* ligases of less than one micromolar; *S. aureus* and *S. pneumoniae* ligase activity were single digit micromolar (see Table 3). The meta-aminomethylbenzylamine analog (i.e., the third compound in Table 3) was found to have Ki's less then 1 μM against 3 of the 4 ligases in the panel. In a similar manner, the last compound in Table 3 was potent against three ligase species. The fourth compound in Table 3, in which the primary amine was substituted with an amidine, showed activity similar to that of the first compound.

TABLE 3

| MOLSTRUCTURE | E. coli ligase Ki/ATP (uM) avg | H. Influenzae ligase Ki/ATP (uM) avg | Staph ligase Ki/ATP (uM) avg | Strep ligase Ki/ATP (uM) avg |
|---|---|---|---|---|
| 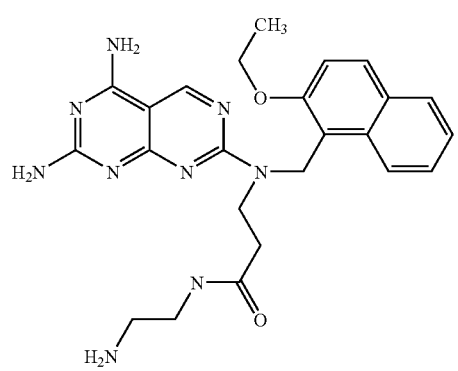 | 0.7 | 1.0 | 4.7 | 1.9 |

TABLE 3-continued

| MOLSTRUCTURE | E. coli ligase Ki/ATP (uM) avg | H. Influenzae ligase Ki/ATP (uM) avg | Staph ligase Ki/ATP (uM) avg | Strep ligase Ki/ATP (uM) avg |
| --- | --- | --- | --- | --- |
| | 9.6 | 0.267 | 9.5 | 3.1 |
| | 5.3 | 0.4 | 0.9 | 0.9 |
| | 1.0 | 0.6 | 6.3 | 1.4 |
| | 1.9 | 1.3 | 3.8 | 4.1 |

TABLE 3-continued

| MOLSTRUCTURE | E. coli ligase Ki/ATP (uM) avg | H. Influenzae ligase Ki/ATP (uM) avg | Staph ligase Ki/ATP (uM) avg | Strep ligase Ki/ATP (uM) avg |
|---|---|---|---|---|
| (structure) | 8.7 | 1.6 | 1.2 | 1.6 |

Carboxylic Acids and Alpha-hydroxy Carboxylic Acids

The first compound in Table 4 was submitted as an HPLC purified mixture of at least two stereoisomers. Protein-ligand crystal structure analysis of this compound showed two stereoisomers, the stereochemistry of which was determined to be (2-R, 1'-S) and (2-S, 1'-R). The number 2 refers to the alpha-hydroxy position, and the number 1, refers to the alpha-methyl position. The two observed isomers are enantiomeric, i.e., they are mirror images. The E. coli ligase potency of the last compound in Table 4 was found to be 143 nM. The compound has a relatively broad spectrum of activity against H. influenzae (566 nM), Staph (4.1 µM), and Strep (2.6 µM).

TABLE 4

| MOLSTRUCTURE | E. coli ligase Ki/ATP (uM) avg | H. Influenzae ligase Ki/ATP (uM) avg | Staph ligase Ki/ATP (uM) avg | Strep ligase Ki/ATP (uM) avg |
|---|---|---|---|---|
| (structure) | 0.611 | — | 7.8 | — |
| (structure) | 5.3 | 3.7 | 6.7 | 2.1 |

TABLE 4-continued

| MOLSTRUCTURE | E. coli ligase Ki/ATP (uM) avg | H. Influenzae ligase Ki/ATP (uM) avg | Staph ligase Ki/ATP (uM) avg | Strep ligase Ki/ATP (uM) avg |
|---|---|---|---|---|
| 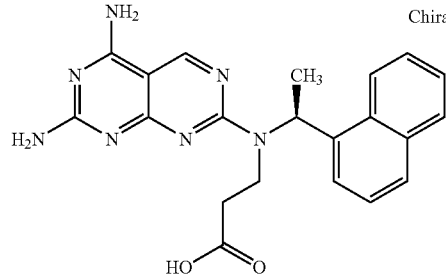 Chiral | 4.2 | 5.7 | 10 | 14.6 |
| 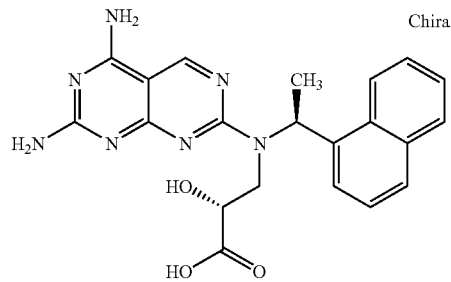 Chiral | 1.4 | 3.5 | 4.3 | 4.3 |
| 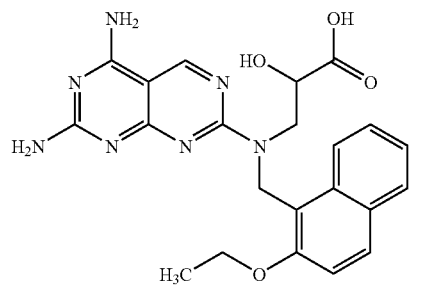 | 0.143 | 0.566 | 4.1 | 2.6 |

N7-primary Butyl Amine SAR

Maximum in vitro potency in this series was identified as that having a butyl amine chain off the N7-nitrogen (i.e., the third compound in Table 5). The alpha-methyl naphthyl chiral center can be replaced with the achiral 2-ethoxynaphthyl substituent (see the fourth compound in Table 5) and still maintain potent ligase activity The achiral molecule has a broader spectrum of ligase activity, and was found to have a Ki of 102 nM against the ligase isolated from $E.\ coli$.

TABLE 5

| MOLSTRUCTURE | E. coli ligase Ki/ATP (uM) avg | H. Influenzae ligase Ki/ATP (uM) avg | Staph ligase Ki/ATP (uM) avg | Strep ligase Ki/ATP (uM) avg |
|---|---|---|---|---|
| 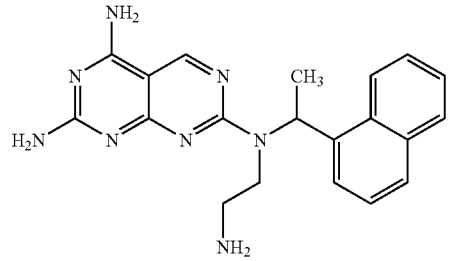 | 2 | 2.7 | 58 | 439 |

TABLE 5-continued
| MOLSTRUCTURE | E. coli ligase Ki/ATP (uM) avg | H. Influenzae ligase Ki/ATP (uM) avg | Staph ligase Ki/ATP (uM) avg | Strep ligase Ki/ATP (uM) avg |
|---|---|---|---|---|
| 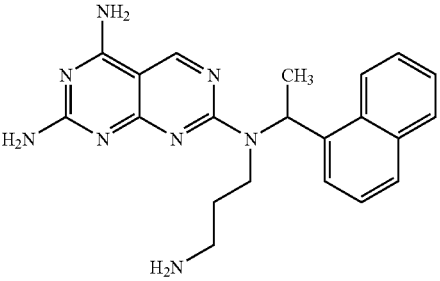 | 0.457 | 5.5 | 46 | 81.2 |
| 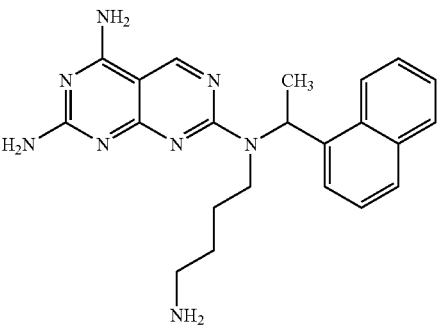 | 0.135 | 4.2 | 32 | 23.1 |
| 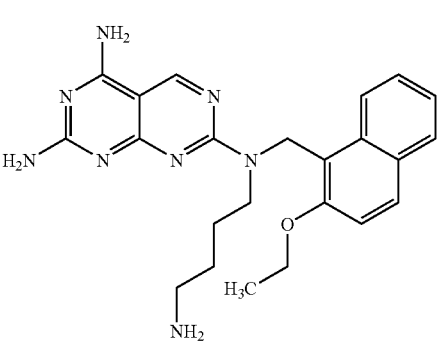 | 0.105 | 0.52 | 15 | 4.5 |
Additional Analogs
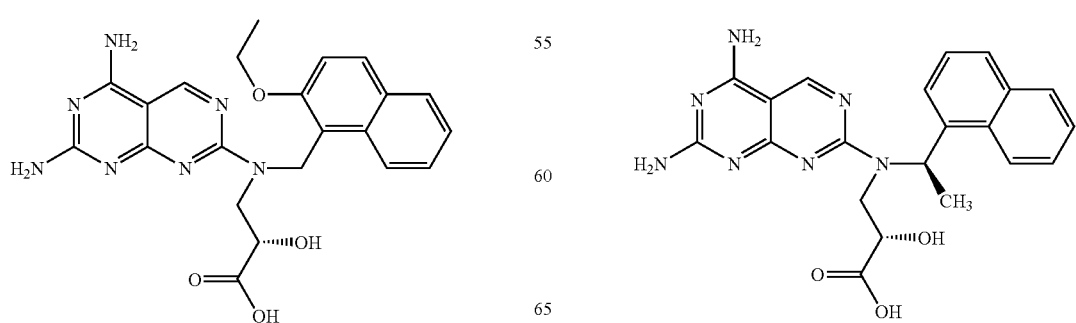

-continued
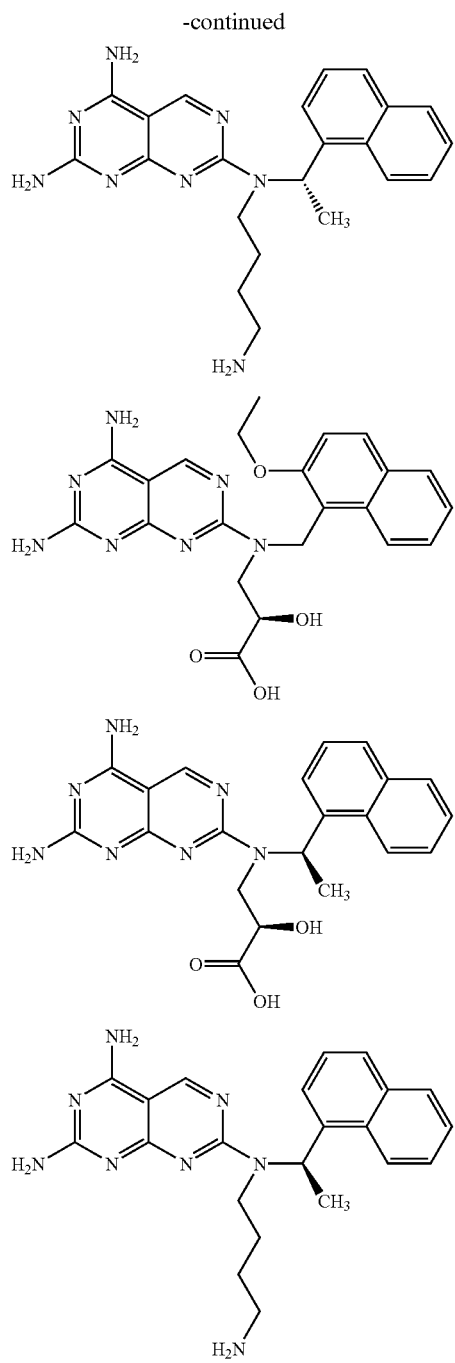
butyl-chain modifications
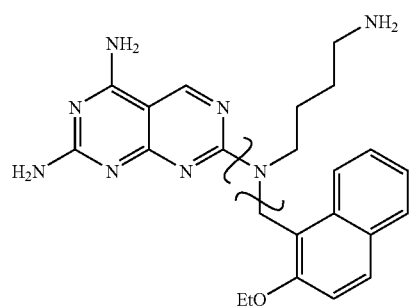
-continued
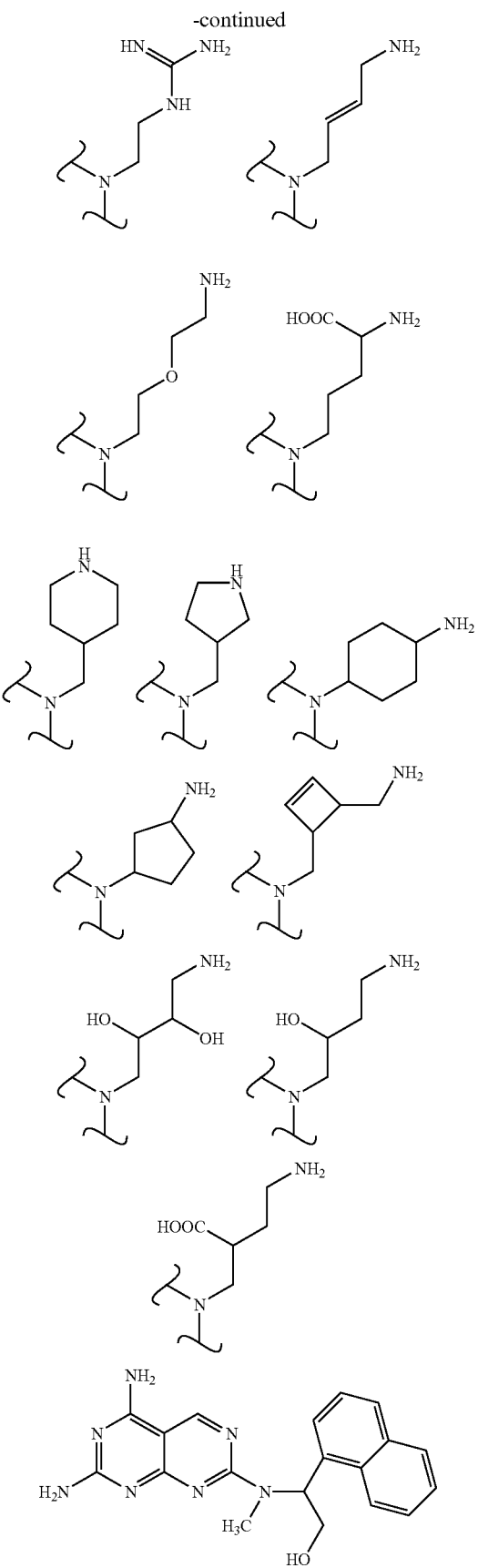

-continued
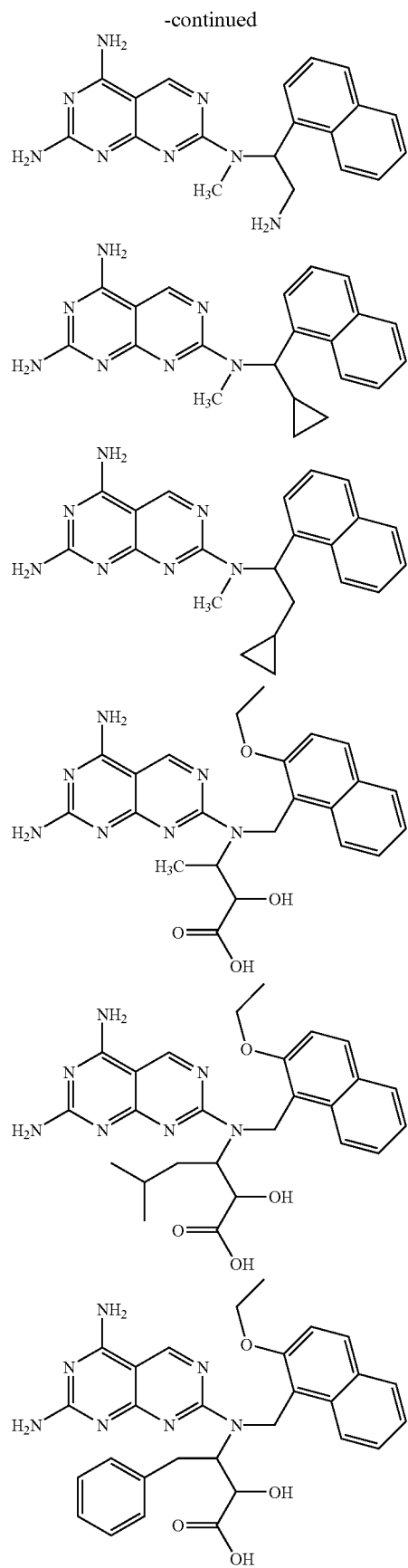
-continued
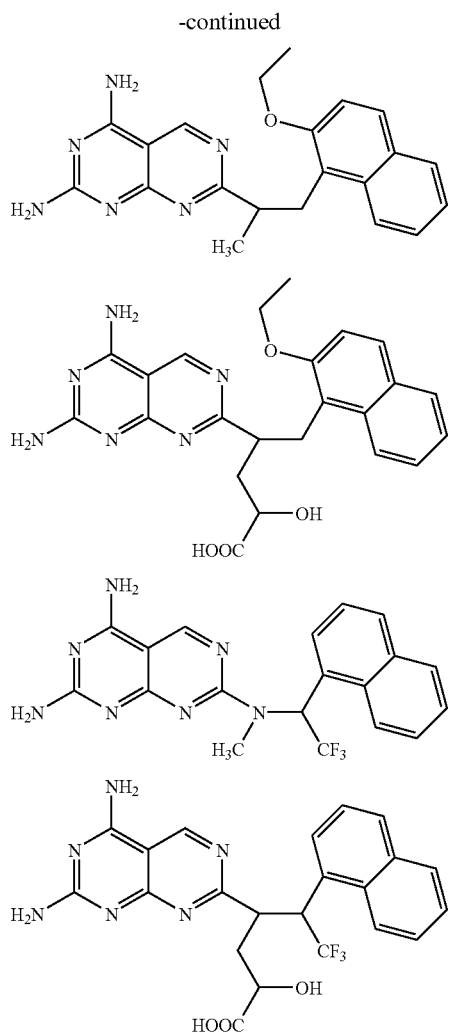
General Synthetic Methodologies Used in the Preparation of Analogs.
Synthesis of Pyrimidopyrimidines
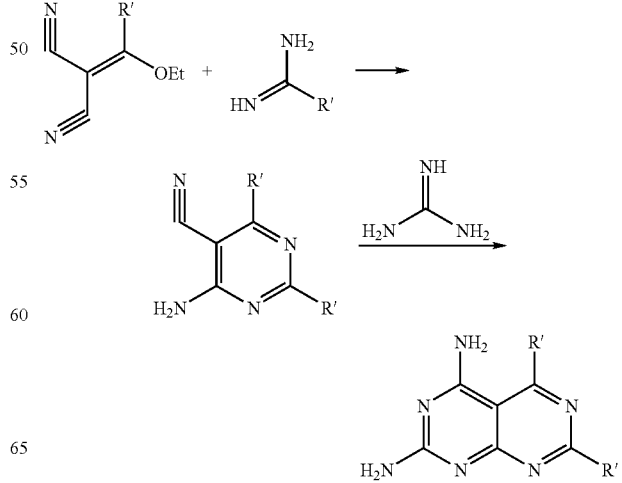

Pyrimidopyrimidine compounds of the invention can be prepared using a variety of synthetic strategies. The pyrimidopyrimidine ring system can be synthesized in a multi-step reaction sequence starting from an appropriately substituted amidine (R7-C=NHNH2) and an R5-substituted alkoxylmethylenemalonitrile. The resulting cyanoaminopyrimidine can be condensed with guanidine to form the pyrimidopyrimine ring system. In the case where R7 in the cyanoaminopyrimidine is either —Cl, —Br, —S-lower alkyl, these leaving groups can be substituted with substituted nitrogen or oxygen nucleuophiles to provide R7-N(or O)-substituted alkyl or aryl intermediates. These intermediates can be cyclized to their corresponding pyrimidopyrimidines with appropriately substituted at the 7-position.

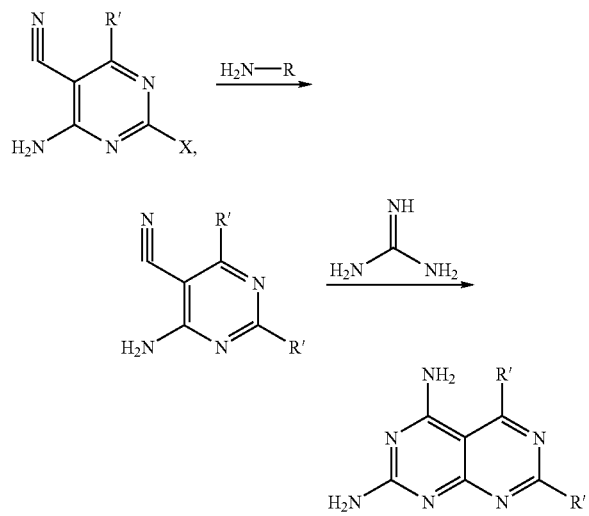

Another method to synthesize 7-aminosubstituted pyrimidopyrimidines is through the nucleophilic attack of amines on 6-amino-2-bromopyrimidine-5-carbonitrile (chloro or thiomethyl, or thioethyl can also be used as leaving groups at the 2-position), and subsequent cyclization of the resulting, appropriately substituted cyanoaminopyrimidine with guanidine.

If the attacking, appropriately substituted nucleophilic amine is not commercially available, then it can be prepared using standard methods in organic chemistry. One such standard method used in preparing compounds in this application is by reductive-amination.

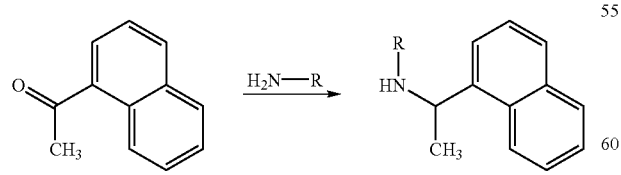

In this well-known procedure, an aldehyde or ketone is condensed with an appropriately substituted amine in the presence of a mild reducing agent such as sodium cyanoborohydride or zinc cyanoborohydride.

Beta-alanine Amides and Alpha-hydroxy-beta-alanine Amides

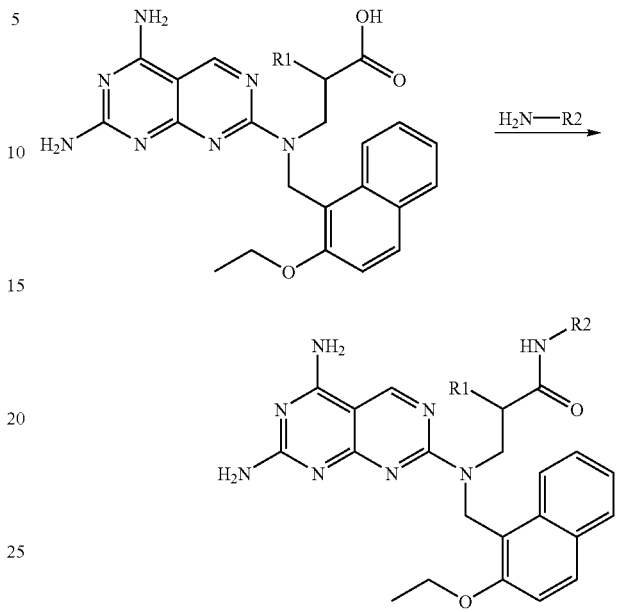

Amides can be synthesized by reaction of their corresponding carboxylic acids with various primary and secondary amines. Addition of numerous reagents described in the literature are useful to facilitate the amide coupling process. Included in these reagents are carbonyldiimidazole (CDI), dicyclohexylcarbodiimide (DCC), HBTU, diethylphosphorocyanidate, and BroP.

Butylamine Analogs

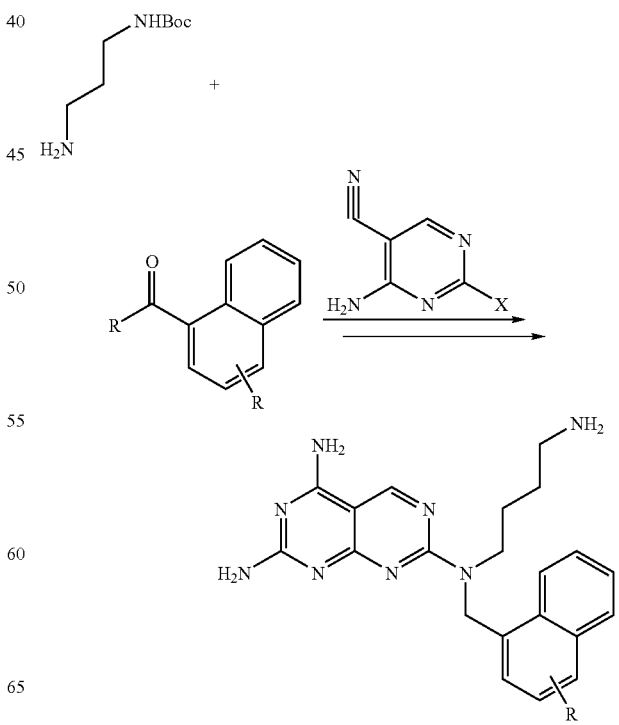

The butylamine analogs were synthesized using a multi-step synthetic pathway. In general, a mono-boc protected butanediamine was reacted under reductive amination conditions to produce an appropriately substituted mono-boc-protected naphthylmethylamine. The secondary amine was reacted with 6-amino-5-cyano-2-halopyrimidine and the resulting intermediate cyclized with quanidine, followed by boc-cleavage under acidic conditions to provide the deprotected butane diamine analogs.

Direct Heterocyclic Substitution Methods

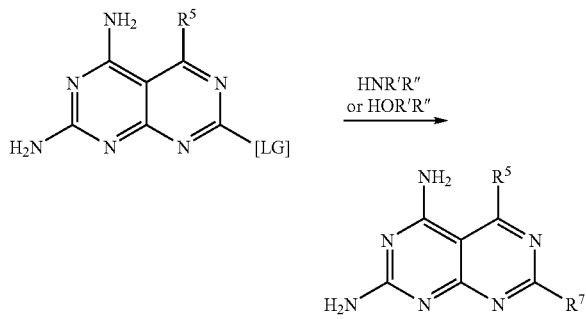

Compounds of the invention can also be prepared by the aromatic nucleophilic displacement of leaving groups on the 7-position of 2,4-diaminopyrimidopyrimidine. These leaving groups [LG] include, but are not limited to: —Cl, —Br, —SCH$_3$, —SC$_2$H$_5$, and —N(CH3)$_3$. The nucleophile used in the displacement reaction can be —N-alkyl, —N-aryl, or substituted alkyl or aryl amines, or —O-alkyl, —O-aryl, or substituted alcohols or phenols.

Synthesis of Pterin Analogs

In general either 6- or 7-substituted pterin analogs can be prepared by the reaction of an activated reagent such as 6- or 7-chloromethyl pterin with nucleophiles such as amines, and by various other methods described in the literature other functional groups at the 6- and 7-position of pterin such as bromomethyl, iodomethyl, hydroxymethyl, activated hydrodroxymethyl, carbonyl, activated carbonyl, hydroxy, chloro, bromo, or methyl can be used as synthetic reagents for the preparation of 6- or 7-substitued analogs.

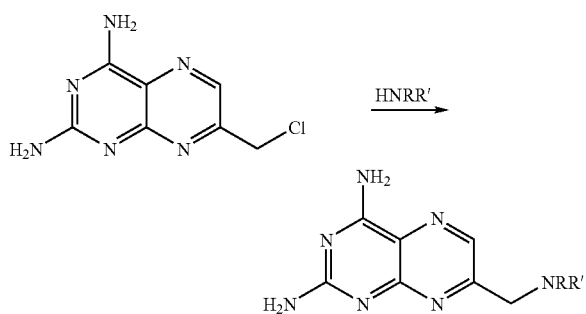

The above general reaction pathway can be used to synthesize a broad range of 7-substituted pteridine analogs. In a general procedure, 7-chloromethyl and an appropriate amine are reacted in an appropriate solvent such as DMF or 2-methoxyethanol for as long as needed as determined by analysis of the reaction mixture by HPLC, TLC, or NMR. The solvent is then removed and the product purified by an appropriate method, usually in the form of precipitation, recrystallization, re-precipitation of the salt by base, or through chromatography.

Formulations, Salt Forms, and Prodrugs

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention that, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or that enhance delivery of the parent compound to a biological compartment (e.g., the brain or lymphatic system) relative to the parent species. Preferred prodrugs include derivatives where a group that enhances aqueous solubility or active transport through the gut membrane is appended to the structure of formulae described herein. In particular, classical examples of ester prodrugs to assist in the absorption and cell membrane penetration of analogs containing free carboxylic acid functional groups can be prepared.

The compounds of this invention can be modified by appending appropriate functionalities to enhance selective biological properties. Such modifications are known in the art and include those that increase biological penetration into a given biological compartment (e.g., blood, lymphatic system, central nervous system), increase oral availability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium, and N(alkyl)$_4^+$ salts. This invention also envisions the quaternization of any basic nitrogen-containing groups of the compounds disclosed herein. Water or oil-soluble or dispersible products may be obtained by such quaternization.

Assays for Inhibition of D-Ala-D-Ala Ligase

Inhibition of D-Ala-D-Ala ligase can be assayed for using the pyruvate kinase/lactate dehydrogenase (PK/LDH) assay described in Example 2, and as described in the literature (e.g., in Sarthy et al., *Anal. Biochem.*, 254:288-290, 1997). In the bacterial cell wall synthesis process, the ligase catalyzes the conversion of adenosine triphosphate (ATP) to adenosine diphosphate (ADP) concurrent with the ligation of two D-alanine residues to form D-alanyl-D-alanine. PK then regenerates ATP from the ADP thus created simultaneously with the conversion of phosphopyruvate to pyruvate. LDH catalyzes the reduction of pyruvate to lactate by converting NADH to $NAD^+$. By monitoring the production rate of $NAD^+$ (e.g., using UV/Vis spectroscopy), D-Ala-D-Ala ligase activity can be ascertained.

Compounds can be screened for % inhibition as described in Example 3.

The inhibition constant Ki and mode of action can be obtained as described in Example 4.

The protein sequence for the enzyme D-ala-D-ala ligase has been determined in a variety of different bacterial species using standard techniques in biochemistry (see Table 5). The protein sequence from any species can be overexpressed in an appropriate host organism such as E. coli using standard molecular biology techniques. The ligase enzyme can be harvested, purified, and used in the above described assay for the determination of inhibitory activity.

In Vitro Assays for Antibacterial Activity

The compounds can be screened for antibacterial activity using standard methods.

In one example, illustrated in Example 5 below, broth microdilution techniques are used to measure in vitro activity of the compounds against a given bacterial culture, to yield minimum inhibitory concentration (MIC) data.

Microdilution Antimicrobial Susceptibility Test Assay

Stock solutions of tested compounds are prepared in N,N-dimethylformamide (DMF) at a concentration of 5 mg/ml. Working solutions of the tested compounds were then prepared from the stock solutions, in Mueller-Hinton broth (MHB) with a starting concentration of 64 µg/ml.

Bacterial inocula were prepared from overnight culture (i.e., one fresh colony from agar plate in 5 ml MHB; H. influenzae was grown in MHB with the addition of yeast extract, haematin, and NAD), centrifuged 2×5 min/3000 rpm (for S. pneumoniae and H. influenzae, 2×10 min/3000 rpm), and dispensed in 5 ml of fresh MHB each time, such that the bacterial suspension is diluted to obtain 100 colony forming units (cfu) in a microplate well (100 µl total volume).

Microplate wells were filled with two-fold dilutions of test compound (50 µl), starting with 64 µg/ml. Wells were then filled with 50 µl of bacterial inoculum (final volume: 100 µl/well). The plates were incubated at 37° C. for 18-24 hours (S. pneumoniae was grown in a $CO_2$-enriched atmosphere).

The optical density of each well at 590 nm ($OD_{590}$) was then measured with a TECAN SpectroFluor Plus®, and minimum inhibitory concentration (MIC) was defined as the concentration that showed 90% inhibition of growth. In one example, illustrated in Example 5, broth microdilution techniques are used to measure in vitro activity of the compounds against a given bacterial culture, to yield minimum inhibitory concentration (MIC) data.

Antimicrobial Agar Dilution Test

This assessment is performed essentially as described in known literature. [See, e.g., NCCLS. Methods for Antimicrobial Susceptibility Testing of Anaerobic Bacteria; Approved Standard-Fourth Edition. NCCLS document M 11-A4. NCCLS: Wayne, Pa.; 1997.]

Agar medium: Brucella blood agar supplemented with hemin (5 µg/ml), 5% sheep blood, and vitamin $K_1$ (1 µg/ml).

Antimicrobial Agents: Standard antimicrobial powders (e.g., azithromycin, chloramphenicol, nitrofurantoin, piperacillin, clindamycin, penicillin, imipenem) and test compound, are prepared as stock solutions [5120 µg/ml in DMF (dimethylformamide)] and diluted as indicated in Table 3 of the NCCLS Methods for Antimicrobial Susceptibility Testing of Anaerobic bacteria; Approved Standard-Fourth Edition 1997; M11-A4, Vol. 17 No 22.

Inoculum Preparation: The test anaerobic strains are selected from enriched Brucella blood agar. Portions of five colonies are directly suspended into Brucella broth medium to achieve a turbidity equivalent to a 0.5 McFarland standard.

Procedure: The medium is prepared according to the manufacturer's directions and distributed into screw-cap tubes. On the day of the test, blood supplement and 2 ml of each concentration of the antimicrobial agent are added to the appropriate tubes of cooled (50° C.) agar. The mixture of media and antimicrobial agent is poured into standard (15× 100 mm) round petri dishes and allowed to solidify. A turbidity-adjusted culture of each anaerobic strain is inoculated to each plate by a replicating device (approximately 2 µl per spot). The inoculated plates are incubated at 35° C. in an anaerobic jar. Results are recorded after 48 hours of incubation and expressed as minimum inhibitory concentration (MIC) values.

In vivo Assays for Antibacterial Activity

The compounds can also be tested for antibacterial efficacy in laboratory animals. These in vivo studies include, but are not limited to, systemic and topical models of infection, urinary tract infection models, sepsis, antibiotic mediated colitis and wound care. The compounds of the invention can also be evaluated in animals to assess their pharmacokinetic profiles, such as oral bioavailability, oral absorption, chemical half-life, identification of metabolites, serum levels at various times, and rate of excretion, for example.

Systemic Bacterial Infection Animal Models

Systemic models of infection are described in the literature. The following conditions can be used to assay the compounds in this application. Bacteria are grown in Mueller-Hinton agar at 37° C. during 24 h. For each experiment, a bacterial suspension is prepared by inoculating 4-5 bacterial colonies onto Mueller-Hinton broth (MHB) and by incubating at 37° C. for 24 hours to yield approximately $10^9$ CFU/ml. BalbC female mice are supplied by Charles River. Animals are infected by a single administration of an $LD_{100}$ dose of bacterial culture suspension ($1\times10^8$ CFU/100 µl per animal) in the tail vein. A careful clinical examination is made several times a day, and obvious clinical symptoms and mortality are recorded. Animals survival is observed for a period of 6 days. Azithromycin is dissolved in 0.5% methocel in saline solution and administered orally. Test compounds are micronized with mortar and pestle and then dissolved in methocel saline solution with 3% of DMF. The first dose is administered 30 minutes after infection, with following doses every 12 hours for 3 days.

Assays for Biochemical and Physical-Chemical Properties

The heterocyclic compounds of this invention can be optimized for their in vitro "antibacterial" activity according to the results of two types of methods, structural methodology and physical-chemical methodology. The chemical structure can be modified using combinations of substituents to provide compounds that satisfy some or all of the following criteria: 1) a compound in which the calculated or experimentally determined lipophilicity (logP) is in the range of 0 to 2 logP units; 2) a compound that is a substrate for any D-Ala-D-Ala ligase enzyme; 3) a compound in which its aqueous solubility is greater than 1 µg/ml. These physical-chemical and biochemical properties are factors in the antimicrobial effects seen in subjects (e.g., animals).

Clinical Uses of the Heterocyclic Compounds

The compounds claimed in this invention can be used therapeutically or prophylactically for treatment or prevention of bacterial infections and/or diseases.

The invention also relates to methods, for example, of disrupting the internal regulation of microbial growth, in a subject, comprising the step of administering to said subject a compound of any of the formulae described herein or a composition comprising a compound of any of the formulae described herein. In one embodiment, the invention relates to a method of inhibiting microbial or bacterial activity in a subject comprising the step of administering a compound to the subject, or a composition comprising a compound, of any one of the formulae described herein. Preferably, the subject is a human being or animal.

In an alternate embodiment, this invention relates to a method of treating disease or disease symptoms in a subject comprising the step of administering to said subject a compound, or a composition comprising a compound, of any of the formulae described herein. Preferably, the subject is a human being or animal.

Infections and infectious diseases are caused from a variety of microorganisms. The compounds of the invention may find use in the medical treatment of infectious diseases from bacterial sources.

Compounds that kill or limit the growth of microorganisms may find use in the treatment of infections and infectious diseases. Specific bacterial microorganisms are known to be associated with the type of infection or infectious disease. Some examples of bacterial infections and their most common causative pathogens are given below.

Upper and lower respiratory tract infections include, but are not limited to: bronchitis, sinusitis, pneumonia, sore throat, chronic streptococcal infections, diphtheria, acute epiglottitis, influenza, chronic bronchitis, middle ear infections (otitis media), pneumonia, bronchopneumonia, Legionnaire's disease, a typical pneumonia, whooping cough, and tuberculosis.

Bacterial microorganisms causing respiratory tract infections include but are not limited to: *S. pyogenes, S. pneumoniae, S. aureus, H. influenzae, M. catarrhalis, N. meningitidis, B. pertussis,* Enterobacteriaceae, anaerobes, *Nocardia, Pseudomonas, C. psittaci,* and *C. diphtheriae.*

Urinary tract infections include, but are not limited to: urethritis, cystitis, pyelonephritis (kidney infection), asymptomatic bacteruria, interstitial cystitis, acute urethral syndrome, and recurrent urinary tract infections.

Bacterial microorganisms causing urinary tract infections include but are not limited to: *E. coli, Proteus, Providentia, Pseudomonas, Klebsiella, Enterobacter, Serratia, Coag. neg. Staphylococci, Enterococci,* and *C. trachomatis.*

Skin and wound infections include, but are not limited to: erythrasma, panaritium, impetigo, folliculitis, erysipelas, cellulitis, and necrotizing fasciitis.

Bacterial microorganisms causing skin and wound infections include but are not limited to: *Streptococci, Staphylococci, P. aeruginosa, P. acnes, Clostridia,* anaerobes, and *B. fragilis.*

Bacterial microorganisms causing systemic infections (bacteremia) include but are not limited to: *Streptococci,* *Staphylococci,* Enterobacteriaceae, *Pseudomonas, Bacteroides* sp., *Neisseria, H. influenzae, Brucella, Listeria,* and *S. typhi.*

Sexually transmitted diseases of bacterial origin include, but are not limited to: adnexitis, cervicitis, chanchroid, urethritis, balanitis, gonorrhea, lymphogranuloma venereum, syphilis, and granuloma inguinale.

Bacterial microorganisms causing sexually transmitted infections include but are not limited to: *Chlamydia, N. gonorrhoeae, U. urealyticum, T. pallidium, G. vaginalis, H. ducreyi, C. granulomatis, Streptococci, Staphylococci,* and Enterobacteriae.

Gastrointestinal infections of bacterial origin include but are not limited to: food borne infections, colitis, enteritis, gastric ulcers, duodenal ulcers, pancreatitis, gall bladder infections, cholera, and thyphus.

Bacterial microorganisms causing gastrointestinal infections include but are not limited to: *H. pylori, C. pylori, C. duodeni, S. typhi, S. paratyphi, V. cholerae,* anaerobes, Enterobacteriaceae, *Staphylococci,* and *Streptococci.*

Methods of Treating Patients

The heterocyclic compounds of the formulae delineated herein can be administered to a patient, for example, in order to treat an infection such as a bacterial infection. The heterocyclic compounds can, for example, be administered in a pharmaceutically acceptable carrier such as physiological saline, in combination with other drugs, and/or together with appropriate excipients. The heterocyclic compounds of the formulae herein can, for example, be administered by injection, intravenously, intraarterially, subdermally, intraperitoneally, intramuscularly, or subcutaneously; or orally, buccally, nasally, transmucosally, topically, in an ophthalmic or otic preparation, or by inhalation, with a dosage ranging from about 0.001 to about 100 mg/kg of body weight, preferably dosages between 10 mg and 5000 mg/dose, every 4 to 120 hours, or according to the requirements of the particular drug.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms. In an alternate embodiment, this invention provides methods of treating, preventing, or relieving symptoms of disease in a mammal comprising the step of administrating to said mammal any of the pharmaceutical compositions and combinations described above. Preferably, the mammal is a human. If the pharmaceutical composition only comprises the compound of this invention as the active component, such methods may additionally comprise the step of administering to said mammal an additional therapeutic agent such as, for example, macrolide antibiotics (e.g., clarithromycin), proton pump inhibitors (e.g., omeprazole), rifamycins (e.g., rifampin), aminoglycosides (e.g., streptomycin, gentamycin, tobramycin), penicillins (e.g., penicillin G, penicillin V, ticarcillin), P-lactamase inhibitors, cephalosporins (e.g., cefazolin, cefaclor, ceftazidime), and antimycobacterial agents (e.g., isoniazid, ethambutol). Other suitable agents are delineated in infectious disease texts and publications, including for example, *Principles and Practice of Infectious Diseases*, G. L. Mandell et al. eds., 3$^{rd}$ ed., Churchhill Livingstone, New York, (1990). Such additional(s) agent may be administered to the mammal prior to, concurrently with, or following the administration of the composition having a compound of any of the formulae herein.

Pharmaceutical compositions of this invention comprise a compound of the formulae described herein or a pharmaceutically acceptable salt thereof; an additional agent selected from an anticancer agent, an antiviral agent, antifungal agent, antibiotic, and any pharmaceutically acceptable carrier, adjuvant or vehicle. Alternate compositions of this invention comprise a compound of the formulae described herein or a pharmaceutically acceptable salt thereof, and a pharmaceutically acceptable carrier, adjuvant or vehicle. Such compositions can optionally also comprise additional therapeutic agents, including, for example an additional agent selected from an anticancer agent, an antimicrobial agent, an antiviral agent, antifungal agent, proton pump inhibitor, or antibiotic. The compositions delineated herein include the compounds of the formulae delineated herein, as well as additional therapeutic agents if present, in amounts effective for achieving a modulation of microbial or bacterial levels.

The term "pharmaceutically acceptable carrier or adjuvant" refers to a carrier or adjuvant that can be administered to a patient, together with a compound of this invention, and that does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. a Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention can be administered orally, parenterally, by inhalation spray, topically, rectally, nasally, buccally, vaginally or via an implanted reservoir, preferably by oral administration or administration by injection. The compositions can be derived from crystalline or non-crystalline forms of the compounds. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions can be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may Is also contain a long-chain alcohol diluent or dispersant, or carboxymethyl cellulose or similar dispersing agents that are commonly used in the formulation of pharmaceutically acceptable dosage forms such as emulsions and or suspensions. Other commonly used surfactants such as Tweens or Spans and/or other similar emulsifying agents or bioavailability enhancers that are commonly used in the manufacture of pharmaceutically acceptable solid, liquid, or other dosage m forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient that is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically transdermal patches are also included in this invention.

The pharmaceutical compositions of this invention may be administered by nasal aerosol or inhalation. Such compositions are prepared according to techniques well-known in the art of m pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The compounds and compositions of this invention are useful as sterilizants, antiseptics, adjuvants in wound dressings (e.g., bandages), and adjuvants in wound cleansing methods (swipes, gavage, etc.).

Dosage levels of between about 0.01 and about 100 mg/kg body weight per day, alternatively between about 0.5 and about 75 mg/kg body weight per day (e.g., between about 10 mg and 5000 mg/dose) of the antimicrobial compounds described herein are useful in a monotherapy and/or in combination therapy for the prevention and treatment of microbial mediated disease. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the subject treated and the particular mode of administration. A typical preparation will contain from about 5% to about 95% active compound (w/w). Alternatively, such preparations contain from about 20% to about 80% active compound. When the compositions of this invention comprise a combination of a compound of the formulae described herein and one or more additional therapeutic or prophylactic agents, both the compound and the additional agent should be present, typically, at dosage levels of between about 10 to 100%, and more preferably between about 10 to 80% of the dosage normally administered in a monotherapy regimen. The additional agents can be administered separately, as part of a multiple dose regimen, from the compounds of this invention. Alternatively, those agents may be part of a single dosage form, mixed together with the compounds of this invention in a single composition.

Other Uses

In an alternate embodiment, the inhibitory compounds described herein may be used as platforms or scaffolds that can be utilized in combinatorial chemistry techniques for preparation of derivatives and/or chemical libraries of compounds. Such derivatives and libraries of compounds have antimicrobial activity and are useful for identifying and designing compounds possessing antimicrobial activity. Combinatorial techniques suitable for utilizing the compounds described herein are known in the art as exemplified by Obrecht, D. and Villalgrodo, J. M., *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, e.g., Czarnik, A. W., *Curr. Opin. Chem. Bio.*, (1997) 1, 60). Thus, one embodiment relates to a method of using the compounds described in the formulae herein for generating derivatives or chemical libraries comprising: 1) providing a body comprising a plurality of wells; 2) providing one or more compounds of the formulae described herein in each well; 3) providing an additional one or more chemicals in each well; 4) isolating the resulting one or more products from each well. An alternate embodiment relates to a method of using the compounds described in the formulae herein for generating derivatives or chemical libraries comprising: 1) providing one or more compounds of the formulae described herein attached to a solid support; 2) treating the one or more compounds of the formulae described herein attached to a solid support with one or more additional chemicals; 3) isolating the resulting one or more products from the solid support. In the methods described above, "tags" or identifier or labeling moieties may be attached to and/or detached from the compounds of the formulae herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms; in such instances, the invention expressly includes all tautomeric forms of the compounds described herein (e.g., alkylation of a ring system may result in alkyation at multiple sites, the invention expressly includes all such reaction products). The compounds may also occur in cis- or trans- or E- or Z-double bond isomeric forms. All such isomeric forms of such compounds are expressly included in the present invention. All crystal forms of the compounds described herein are expressly included in the present invention.

The invention will be further described in the following examples. It should be understood that these examples are for illustrative purposes only and are not to be construed as limiting this invention in any manner.

EXAMPLES

Liquid chromatographic data was obtained using a Hewlett-Packard (HP) 1090 Series Liquid Chromatograph coupled to a Diode Array Detector [Restek Allure C18 Column; particle size, 5 μM; column length, 150 mm; column diameter, 4.6 mm; flow rate, 1 ml/min; Solvent program, from 95% $H_2O$ (w/0.1% TFA)/5% $CH_3CN$ (w/0.1% TFA) to 100% $CH_3CN$ (w/0.1% TFA) in 8 minutes, then held constant for 3 minutes; detection wavelength, 254 nm]. Mass Spectral data were obtained on either an Agilent 1100 LC/MS or Thermofinigan AQA/Gilson LC/MS system. $^1$H- and $^{13}$C-NMR spectra were obtained on a Bruker AC-300 MHz instrument.

Medium pressure flash chromatography was performed on an Isco Inc., Combiflash Sg100c system. Thin-layer chromatography was performed using EM Science silica gel 60 F$_{254}$ plastic TLC plates. Melting points were determined in open-air capillary tubes in a Meltemp II apparatus. UV light was used for detecting compounds on the TLC plates. Reagents used in reactions were purchased from the Aldrich Chemical Co. (Milwaukee, Wis.), Sigma Chemical Co. (Saint Louis, Mo.), Fluka Chemical Corp. (Milwaukee, Wis.), Fisher Scientific (Pittsburgh, Pa.), TCI America (Portland, Oreg.), Transworld Chemicals, Inc. (Rockville, Md.), Maybridge Chemical Ltd., (London, England) or Lancaster Synthesis (Windham, N.H.).

Example 1

Synthesis of Ligase Inhibitors

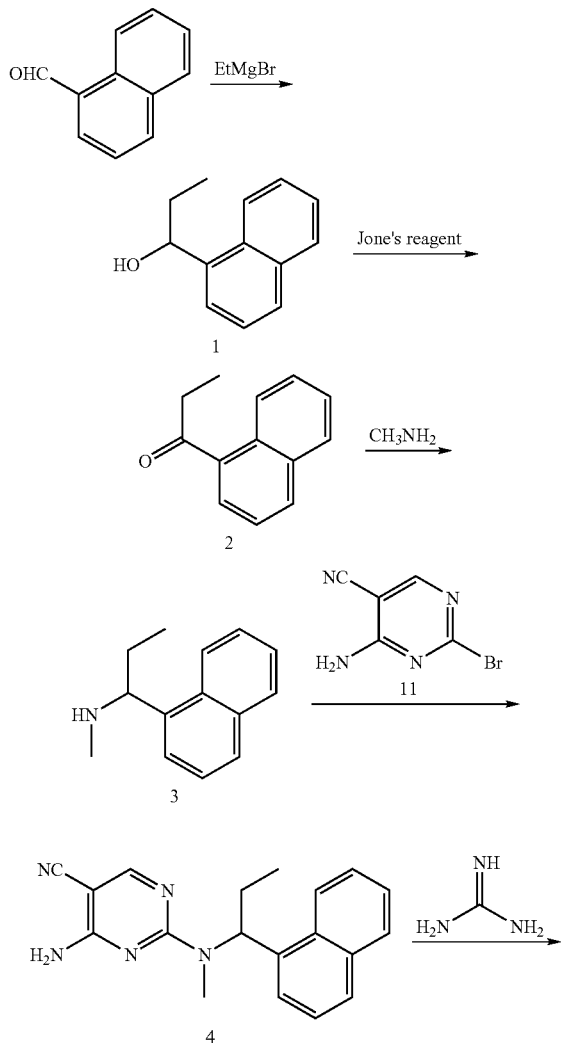

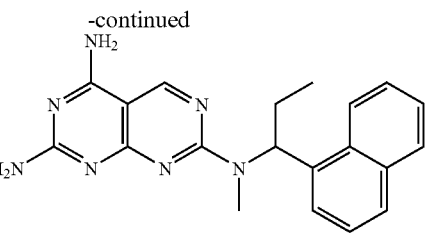

N7-Methyl-N-7-(1-nanhthalen-1-yl-nropyl)-pyrimido[4,5-d]pyrimidine-2,4,7-triamine Compound 1: To a solution of 4.25 g (27.2 mmol) naphthaldehyde in 30 ml dry ether in ice water bath was slowly added 13 ml of ethylmagnesium bromide, 3 M in ether. The mixture was stirred for another 30 min at room temperature and then quenched by adding 40 ml of 1N HCl solution. The organic layer was washed with water (20 ml), sat. sodium bicarbonate (20 ml×2), brine (20 ml) and then dried over anhydrous sodium sulfate. Evaporation of the organic solvent gave a crude product 1 which was directly used for the next step of the reaction without further purification.

Compound 2: The crude product 1 was dissolved in 30 ml acetone and to the resulting mixture, bathed in an ice water bath, was slowly added Jone's reagent until the brown color persisted. The solution was further stirred for 15 min at room temperature and then 5 ml of isopropanol was added. After 50 ml of ethyl acetate was added, the resulting mixture was washed with water (30 ml), sat. sodium bicarbonate (30 ml×2), sat. NaCl and then dried over anhydrous sodium sulfate. Evaporation of the organic solvents gave an oily residue which was then purified by silica gel column chromatography. 4.01 g of ketone 2 was obtained.

Compound 3: To the mixture of 4.01 g ketone 2 and 16.3 ml of methylamine in methanol, 2 M, was added 1.61 g sodium cyanoborohydride and 160 mg of zinc chloride. The resulting mixture was stirred overnight at 50° C. Adding 1N HCl quenched the reaction. After most of the methanol was removed in vacuo, the solution was extracted with dichloromethane (15 ml×2). The pH of the aqueous layer was adjusted to about 9 with 2 N NaOH. The product was then extracted with dichloromethane (15 ml×3). The combined organic layer was washed with sat. NaCl and then dried over anhydrous sodium sulfate. Evaporation of the solvent gave 3.54 g of compound 3.

Compound 4: A mixture of 2.89 g (14.5 mmol) pyrimidine 11, 3.54 g (15 mmol) of compound 3 and 2.5 ml (18 mmol) triethylamine in 25 ml of 2-methoxyethanol was stirred at 80° C. for 2 h. The resulting mixture was cooled down to room temperature and the solvent was evaporated to give an oily residue. 30 ml of ethyl acetate was added to dissolve the residue and the resulting solution was washed three times with water then dried over anhydrous sodium sulfate. Evaporation gave an oily residue, which was then purified by silica gel column chromatography. 3.95 g of product 4 was obtained as white powder.

N7-Methyl-N-7-(1-naphthalen-1-yl-nropyl)-pyrimido[4,5-d]pyrimidine-2,4,7-triamine:

To a solution of 3.60 g of compound 4 in 40 ml of 2-methoxyethanol was added 24 ml of 1M guanidine in methanol and 16 ml of 1.5 M CH$_3$ONa in CH$_3$OH. The mixture was stirred at 140° C. for 12 h with an equipped Dean-Stark trap to remove the methanol solution. The reaction mixture was cooled down and evaporated in vacuo to give an oily residue, which was then dissolved in 30 ml of methanol. 50 ml of water was added to precipitate the product. The product was then purified by recrystallization from methanol, and the recrystallized product was then stirred in methanol three times. 1.95 g of the product was obtained as white powder. The purity of it was greater than 99% based on HPLC analysis.

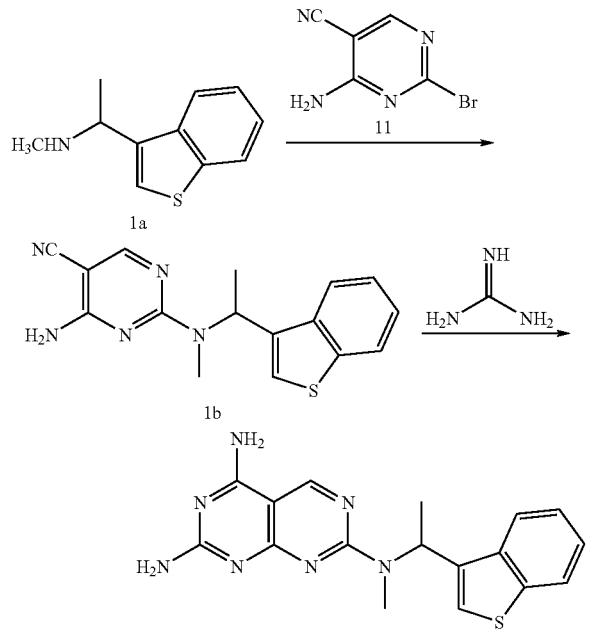

N7-(1-Benzo[b]thiophen-3-yl-ethyl)-N-7-methyl-pyrimido[4,5-d]pyrimidine-2,4,7-triamine A mixture of 2.89 g (14.5 mmol) pyrimidine 11, 2.87 g (15 mmol) methylamine 1 a and 2.5 ml (18 mmol) triethylamine in 25 ml of 2-methoxyethanol was stirred at 80° C. for 2 h. The reaction mixture was cooled down to room temperature and the solvent was evaporated to give a oily residue. 30 ml of ethyl acetate was added to dissolve the residue and the resulting solution was washed three times with water then dried over sodium sulfate. Evaporation gave an oily residue, which was then purified via the recrystallization from ether/hexane. 3.95 g of product 1b was obtained as white powder.

To a solution of 3.71 g 1a in 40 ml of 2-methoxyethanol was added 24 ml of 1M guanidine in methanol and 16 ml of 1.5 M CH₃ONa in CH₃OH. The mixture was stirred at 140° C. for 12 h with an equipped Dean-Stark trap to remove the methanol solution. The reaction ii mixture was cooled down and evaporated in vacuo to give an oily residue, which was then dissolved in 30 ml of methanol. 50 ml of water was added to precipitate the product. The product was then purified by the recrystallization from methanol, then stirring in methanol three times. 920 mg of product was obtained as white powder. The purity of it was 98.52% based on HPLC analysis.

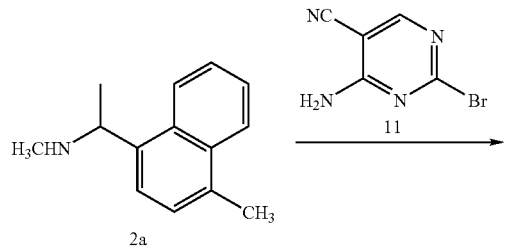

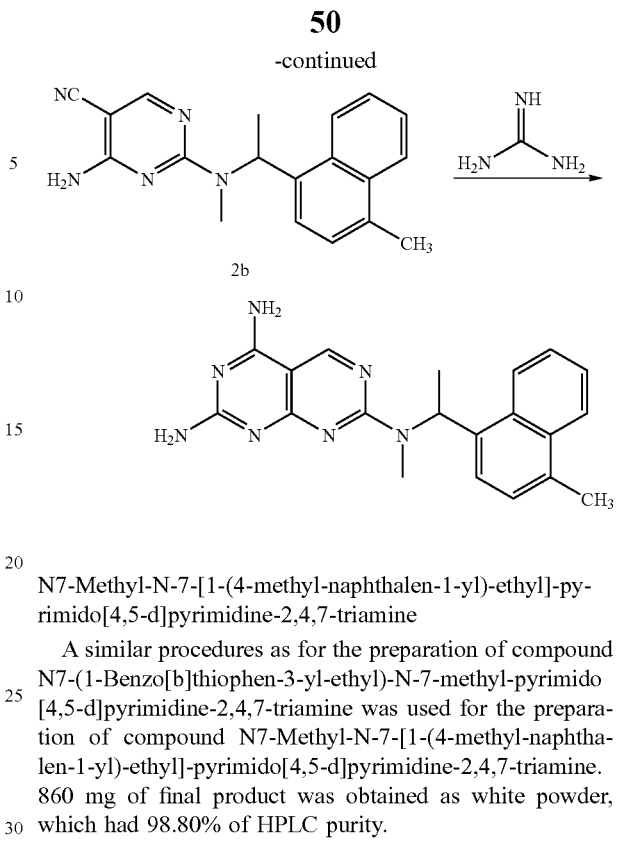

N7-Methyl-N-7-[1-(4-methyl-naphthalen-1-yl)-ethyl]-pyrimido[4,5-d]pyrimidine-2,4,7-triamine A similar procedures as for the preparation of compound N7-(1-Benzo[b]thiophen-3-yl-ethyl)-N-7-methyl-pyrimido[4,5-d]pyrimidine-2,4,7-triamine was used for the preparation of compound N7-Methyl-N-7-[1-(4-methyl-naphthalen-1-yl)-ethyl]-pyrimido[4,5-d]pyrimidine-2,4,7-triamine. 860 mg of final product was obtained as white powder, which had 98.80% of HPLC purity.

Synthesis of 7-Amino Substituted Pyrimidopyrimidines (Structure IV)

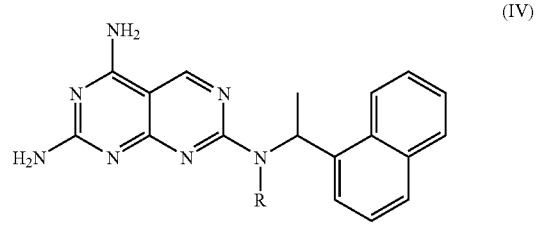

The amines (structure II) were prepared by reductive amination of 1-acetonaphthone with corresponding amines (scheme 2) structure II.

Scheme 2

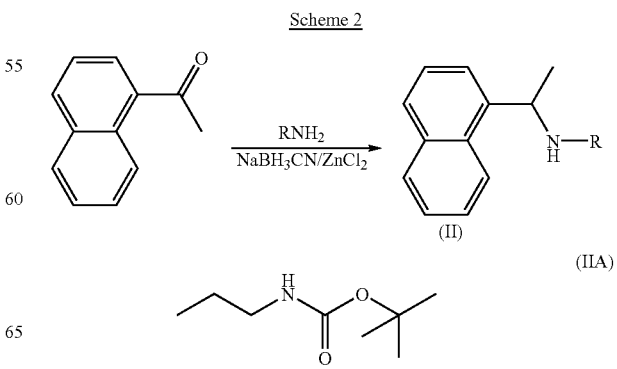

-continued (IIB)

R =

(IIC)

(II A) Tert-butyl N-(2-{[1-(1-naphthyl)ethyl]amino}ethyl) carbamate

To a solution of 1-acetonaphthone (152 µl, 1 mmol) in acetonitrile (2 ml) was added tert-butyl N-(2-aminoethyl)-carbamate (189 µl, 1.2 mmol), NaBH$_3$CN (126 mg, 2 mmol) and anhydrous ZnCl$_2$ (136 mg, 1 mmol). The reaction was heated over night at 80° C. in a screw cap vial with magnetic stirring. The precipitate was filtered off and the solution was evaporated. The residue was dissolved in 3 ml 0.1N HCl and extracted with methylenchloride (2×5 ml). The combined organic layers were dried (na$_2$so$_4$) and evaporated. The crude product was purified by silica gel (sp) chromatography using 1. CH$_2$Cl$_2$ and 2. CH$_2$Cl$_2$/MeOH (10/0.1) as an eluent to give a white waxen product 77%. The structure characterization of the products was made with $^1$HNMR; $^{13}$CNMR; MS (m/z): 315 (MH$^+$).

(II B) Tert-butyl-N-(2-{[1-(1-naphthyl)ethyl]amino}propyl) carbamate

To a solution of 1-acetonaphthone (152 µl, 1 mmol) in acetonitrile (2 ml) was added tert-butyl N-(3-aminopropyl)-carbamate (209 µl, 1.2 mmol), NaBH$_3$CN (126 mg, 2 mmol) and anhydrous ZnCl$_2$ (136 mg, 1 mmol). The reaction was heated for 70 hours at 80° C. in a screw cap vial with magnetic stirring. The precipitate was filtered off and the solution was evaporated. The residue was dissolved in 3 ml 0.1N HCl and extracted with methylenchloride (1×5 ml). The organic layer was dried (Na$_2$SO$_4$) and evaporated. The crude product was purified by silica gel flash chromatography using 1. CHCl$_2$/MeOH (10/0.1) and 2. CH$_2$Cl$_2$/MeOH (10/1), as an eluent, to give an oily product 70%. The structure characterization of the products was made with $^1$HNMR; $^{13}$CNMR; MS (m/z): 329 (MH$^+$).

(II C) Tert-butyl-N-(2-{[1-(1-naphthyl)ethyl]amino}butyl) carbamate

To a solution of 1-acetonaphthone (152 µl, 1 mmol) in acetonitrile (2 ml) was added N-Boc-1,4-diaminobutane (229 µl, 1.2 mmol), NaBH$_3$CN (126 mg, 2 mmol) and anhydrous ZnCl$_2$ (136 mg, 1 mmol). The reaction was heated for 55 hours at 80° C. in a screw cap vial with magnetic stirring. The precipitate was filtered off and the solution was evaporated. The residue was dissolved in 3 ml 0.1N HCl and extracted with methylenchloride (1×5 ml). The organic layer was dried (Na$_2$SO$_4$) and evaporated. The crude product was purified by silica gel flash chromatography using 1. CH$_2$Cl$_2$/MeOH (10/0.1) and 2. CH$_2$Cl$_2$/MeOH (10/1), as an eluent, to give an oily product 80%. The structure characterization of the products was made with $^1$HNMR; $^{13}$CNMR; MS (m/z): 343 (MH$^+$).

Scheme 3

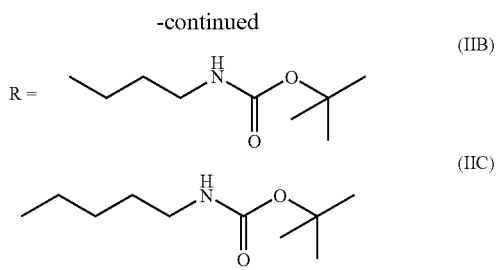

III A 4-Amino-2-{[4-aminoethyl)[1-naphthyl)ethyl]amino}-5-pyrimidinecarbonitrile 4-amino-2-bromopyrimidine-5-carbonitrile (1 mmol, 199 mg), tert-butyl n-(2-{[1-(1-naphthyl)ethyl]amino}ethyl)carbamate (IIA) (1.2 mmol, 377 mg), N,N-diisopropylethylamine (DIEA) (2 mmol, 342 µl) and 2-methoxyethanol (2 ml) were placed in screw cap vial and heated at 150° C. for 4 hours. 2-methoxyethanol was evaporated. The residue was dissolved in 3 ml 0.1N HCl and extracted with methylenchloride (2×5 ml). The combined organic layers were dried (Na$_2$SO$_4$) and evaporated. The crude product was purified by silica gel (sp) chromatography using CH$_2$Cl$_2$/MeOH (10/0.1), as an eluent, to give a white amorphous product.

To the amorphous product was added a cold solution of 50% trifluoroacetic acid in dichloromethane (1 ml) and the mixture agitated for 1 hour at room temperature. The solution was evaporated. To the crude product was added saturated solution of na$_2$co$_3$ and extracted with methylenchloride (2×5 ml). The organic layers were dried (Na$_2$SO$_4$) and evaporated. Yielded: 36% white solid. The structure characterization of the products was made with $^1$HNMR; $^{13}$CNMR; MS (m/z): 333 (MH$^+$).

III B 4-Amino-2-{[4-aminopropyl)]1-naphthyl)ethyl] amino}-5-pyrimidinecarbonitrile 4-amino-2-bromopyrimidine-5-carbonitrile (1 mmol, 199 mg), tert-butyl N-(2-{[1-(1-naphthyl)ethyl]amino}propyl) carbamate (IIB) (1.2 mmol, 394 mg), N,N-diisopropylethylamine (diea) (2 mmol, 342 µl) and 2-methoxyethanol (2 ml) was placed in screw cap vial and heated at 150° C. for 5 hours. 2-metoxyethanol was evaporated. The residue was dissolved in 3 ml 0.1N HCl and extracted with methylenchloride (2×5 ml). The combined organic layers were dried (Na$_2$SO$_4$) and evaporated. The crude product was purified by silica gel (sp) chromatography using CH$_2$Cl$_2$/MeOH (10/0.1) as an eluent to give a white amorphous product.

To the amorphous product was added a cold solution of 50% trifluoroacetic acid in dichloromethane (2 ml) and the mixture agitated for 1 hour at room temperature. The solution was evaporated. To the crude product was added saturated solution of $Na_2CO_3$ and extracted with methylchloride (2×5 ml). The organic layers were dried ($Na_2SO_4$) and evaporated. Yielded: 66% white solid. The structure characterization of the products were made with $^1$HNMR; $^{13}$CNMR; MS (m/z): 347 (MH$^+$).

III C4-Amino-2-{[4-aminobutyl)[1-naphthyl)ethyl]amino}-5-pyrimidinecarbonitrile 4-amino-2-bromopyrimidine-5-carbonitrile (1 mmol, 199 mg), tert-butyl N-(2-{[1-(1-naphthyl)ethyl]amino}butyl) carbamate (IIC) (1.2 mmol, 410 mg), N,N-diisopropylethylamine (DIEA) (2 mmol, 342 μl) and 2-methoxyethanol (2 ml) was placed in screw cap vial and heated at 150° C. for 4 hours. 2-metoxyethanol was evaporated. The residue was dissolved in 3 ml 0.1N HCl and extracted with methylenchloride (2×5 ml). The combined organic layers were dried ($Na_2SO_4$) and evaporated. The crude product was purified by silica gel (sp) chromatography using $CH_2Cl_2$/MeOH (10/0.1) as an eluent to give a white amorphous product.

To the amorphous product was added a cold solution of 50% trifluoroacetic acid in dichloromethane (1.5 ml) and the mixture agitated for 1 hour at room temperature. The solution was evaporated. To the crude product was added saturated solution of $Na_2CO_3$ and extracted with methylenchloride (3×5 ml). The organic layers were dried ($na_2so_4$) and evaporated. Yielded: 54% white solid. The structure characterization of the products was made with $^1$HNMR; $^{13}$CNMR; MS (m/z): 361 (MH$^+$).

The forming 7-substituted pyrimido pyrimidines (structure IV) was carried out by the condensation of 2-substituted 2,4-diamino-5-pyrimidinecarbonitriles (structure III) with guanidine (scheme 4).

Scheme 4

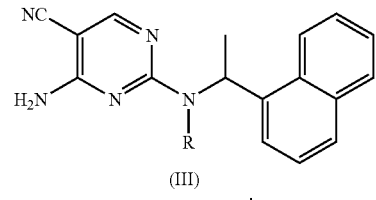
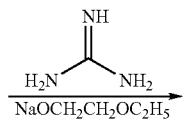

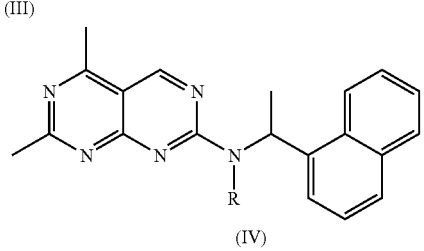

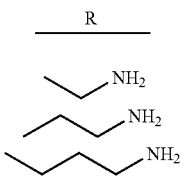

Compound IVC

4-Amino-2-{[4-aminobutyl)[1-naphthyl)ethyl]amino}-5-pyrimidinecarbonitrile (IIIC) (0.26 mmol, 95 mg) was dissolved in 1.2 ml of the guanidine free base (the preparation see below) in 2-methoxyethanol. The reaction mixture was stirred in screw cap vial at 150° C. for 1.5 hours. 2-metoxyethanol was evaporated. The water was added and the precipitate was filtered and the crude product was purified by silica gel (sp) chromatography using $CH_2Cl_2$/MeOH/$NH_3$ (2/1/0.1) as an eluent to give a white solid 42%. The structure characterization of the products were made with 113; CNMR; MS (m/z): 403 (MH$^+$).

Compound IVB

4-Amino-2-{[4-aminopropyl)[1-naphthyl)ethyl]amino}-5-pyrimidinecarbonitrile (IIB) (0.26 mmol, 93 mg) was dissolved in 1.3 ml of the guanidine free base (the preparation see below) in 2-methoxyethanol. The reaction mixture was stirred in screw cap vial at 150° C. for 1.5 hours. 2-metoxyethanol was evaporated. The water was added and the precipitate was filtered and the crude product was purified by silica gel (sp) chromatography using $CH_2Cl_2$/MeOH/$NH_3$ (2/1/0.1) as an eluent to give a white solid 38%. The structure characterization of the products were made with $^1$HNMR; $^{13}$CNMR; MS (m/z): 389 (MH$^+$).

Compound IVA

4-Amino-2-{[4-aminoethyl)[1-naphthyl)ethyl]amino}-5-pyrimidinecarbonitrile (IIIA) (0.3 mmol, 100 mg) was dissolved in 1.4 ml the guanidine free base (the preparation see below) in 2-methoxyethanol. The reaction mixture was stirred in screw cap vial at 150° C. for 1.5 hours. 2-metoxyethanol was evaporated. The water was added and the precipitate was filtered and the crude product was purified by silica gel (sp) chromatography using $CH_2Cl_2$/MeOH/$NH_3$ (10/2/0.2) as an eluent to give a white solid 46%. The structure characterization of the products was made with $^1$HNMR; $^{13}$CNMR; MS (m/z): 375(MH$^+$).

The Preparation of the Guanidine Free Base in 2-Methoxyethanol

In a separate container sodium metal (1 g, 44 mmol) was added to 30 ml of 2-methoxyethanol, stirred under an inert atmosphere until no sodium metal was observed in solution.

In a separate container was made a guanidine hydrochloride (4.2 g, 44 mmol) solution in 2-methoxyethanol (30 ml). To this solution was added the sodium methoxyethoxide solution. Upon addition a white precipitate was formed (NaCl). The reaction was stirred at 25° C. for 30 minutes. The precipitate was filtered and the solution was stored in refrigerator and used as a solution of guanidine free base.

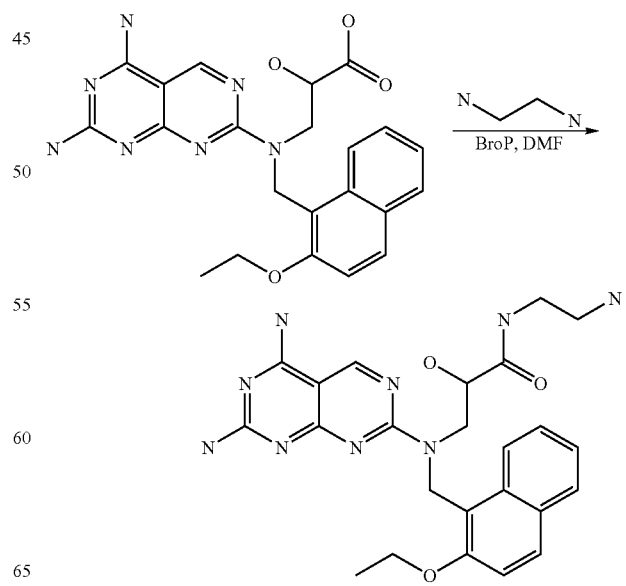

3-[(5,7-Diamino-pyrimido[4,5-d]pyrimidin-2-yl)-(2-ethoxy-naphthalen-1-ylmethyl)-amino]-2-hydroxy-propionic acid The alpha-hydroxy carboxylic acid was synthesized in a multi-step procedure starting from isoserine, using experimental methods and conditions similar to those described in detail elsewhere in this application. The enantiomeric alcohols can be synthesized stereoselectively utilizing the reaction of 2-ethoxynaphthylmethylamine on esters of glycinic acid (epoxide).

N-(2-Amino-ethyl)-3-[(5,7-diamino-pyrimido[4,5-d]pyrimidin-2-yl)-(2-ethoxy-naphthalen-1-ylmethyl)-amino]-2-hydroxy-propionamide To 3-[(5,7-diamino-pyrimido[4,5-d]pyrimidin-2-yl)-(2-ethoxy-naphthalen-1-ylmethyl)-amino]-2-hydroxy-propionic acid (200 mg, 0.445 mmol) in dry DMF (2 ml) was added BroP (249 mg, 0.534 mmol). After the mixture was stirred for 30 min, DIEA (126 mg, 0.979 mmol) was added. After stirring for another 20 min, ethylene diamine (53.5 mg, 0.89 mmol) was added. The mixture was then stirred at room temperature for 16 hours and was directly purified by prep HPLC to yield 35 mg (16%) of the title compound: MS m/z (M+H) 492.

General Procedure Used Reacting Various Amines with Aromatic Ketones Under Reducing Conditions

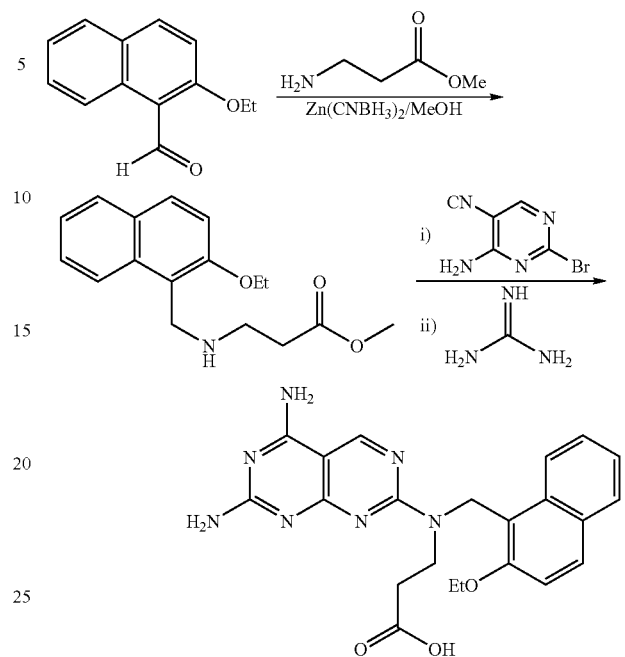

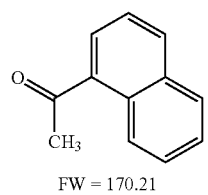

The following procedure is based on a literature method (*J. Org. Chem.* 1985, 50, 1927-1932).

At room temperature, to a solution of 1-acetylnaphthylene (1 equiv, 1 mmol, 170 mg, 151 µl) in methanolic methylamine solution (4 equiv, 4 mmol, 2 ml of 2 M in methanol) was added solid sodium cyanoborohydride (2 equiv, 2 mmol, 126 mg) and anhydrous zinc chloride (1 equiv, 1 mmol, 136 mg). The reactions were heated to 65° C. in an open tube with magnetic stirring.

The course of the reaction can be monitored by either TLC or HPLC. At 30 min, several peaks were observed. An authentic sample of N-methyl-1-naphthylethylamine was used for comparison. At 1 hour, the reaction was >50% complete. At 4 hours the ketone had completely 153 disappeared and the product was 95+% pure, contaminated with only <5% intermediate imine. Heating the reaction longer may have resulted in a cleaner product. We recommend the reaction time of at least 6 hours for this specific ketone, although reaction time may vary dependent on the nature of the ketone. These reactions were worked up in the usual manner and the crude products were purified using standard laboratory techniques.

3-[(5,7-Diamino-pyrimido[4,5-d]pyrimidin-2-yl)-(2-ethoxy-naphthalen-1-ylmethyl)-amino]-propionic acid

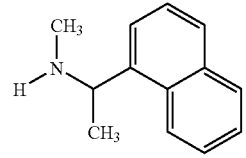

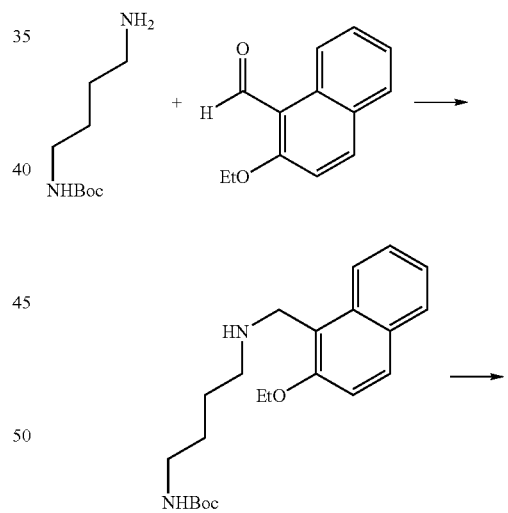

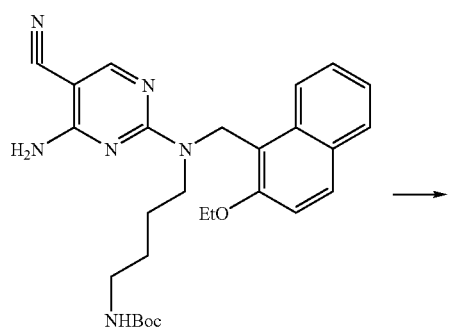

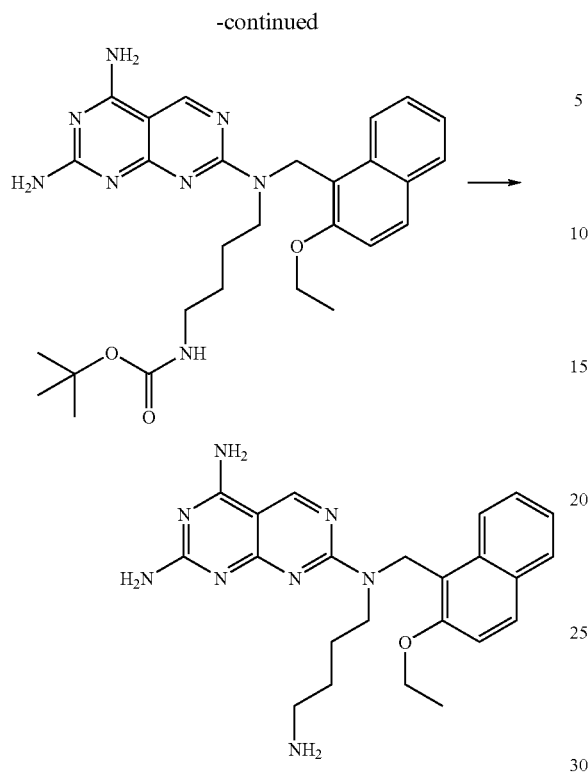

{4-[(5,7-Diamino-pyrimido[4,5-d]pyrimidin-2-yl)-(2-ethoxy-naphthalen-1-ylmethyl)-amino]-butyl}-carbamic acid tert-butyl ester A suspension of the substituted-cyanoaminopyrimdine (12.37 g, 0.025 mol), guanidine hydrochloride (7.16 g, 0.075 mol), solid sodium methoxide (5.40 g, 0.1 mol) in methoxyethanol (150 ml) was heated to reflux for 48 hours. The reaction was determined to be complete by monitoring by HPLC. The reaction mixture was cooled to room temperature and poured into excess water. The solid material was collected on a filter, dried under vacuum, to provide 13.05 grams of crude material that was used in the next step without further purification.

N7-(4-Amino-butyl)-N-7-(2-ethoxynaphthalen-1-ylmethyl-pyrimido[4,5-d]pyrimidine-2,4,7-triamine The mono-bon-protected intermediate (13 g) was added slowly over a period of 10 min to ice cold trifluoroacetic acid (75 ml) with rapid stirring. The reaction was complete as observed by HPLC/MS analysis of an aliquot. The reaction mixture was poured into an ice cold solution of sodium ethoxide (5%) to precipitate the product. The HPLC product was collected on a filter and dried to provide 8.0 grams of solid: HPLC Rt=2.882 min, 99% pure, MS m/z 433 (pos).

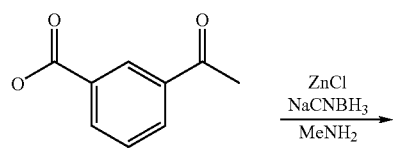

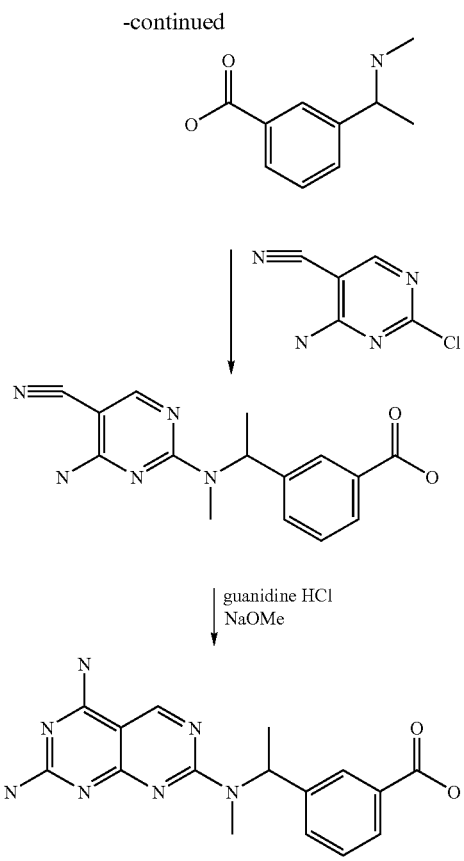

Step 1: Reductive Amination 20.0 g (0.12 mole) of the ketone was dissolved in 100 ml (~2 eq.) of a 2M methanolic solution of methylamine. In a separate flask cooled to 0° C. was added 8.3 g (0.5 eq.) of ZnCl₂ and 7.7 g (1.0 eq.) NaCNBH₃ in about 10 ml of MeOH. The Zn(CNBH₃)₂ was allowed to mix at 0 degrees for about 5 minutes and then added as a slurry to the ketone/amine mixture. The reaction was brought to a gentle reflux overnight. The reaction was allowed to cool to room temp. and rotovaped to dryness. The material was allowed to sit under high vacuum in order to remove any residual methylamine.

The white solid was triturated with Et₂O however, a viscous oil resulted. Better results were observed by trituration with Et₂O by adding enough MeOH to keep the material from oiling out. The material was filtered and washed with ether and allowed to air dry. TLC of the solid versus an authentic sample provided by ET showed identical mobility. Based on weight however, recovery was >100% and it was assumed that inorganic salts were still present.

Due to the contaminating salts present, a small amount of the material was used in the next step. No obvious problems were observed. The amino acid was therefore used without further purification.

Step 2: Reaction with Cl-Pyrimidine 25 g (theoretical yield 21.8 g) of the amino acid was dissolved in approximately 50 ml of ethoxyethanol. To this was added 17.0 g (0.9 eq. based on ketone) of 4-amino-2-chloropyrimidine-5-carbonitrile and 42 ml (2.0 eq.) of DIEA and the reaction was allowed to mix for about 2 hrs. at 80 degrees (temp of oil bath). TLC showed none of the chloride remaining. The reaction was allowed to cool to room temp and the concentrated to about 10 ml on a rotary evaporator. The resulting slurry was diluted with about 400 ml of water and the pH was adjusted to 5-6 (pH paper) using conc. HOAc, at which point a light yellow solid formed. The material was allowed to sit at 0 degrees overnight, filtered and washed with about 1 L of water and air dried. Recrystallization from H$_2$O/MeOH provided ~25 g of the intermediate (69%). TLC (CH$_2$Cl$_2$ 10% MeOH) R$_f$~0.1. There did appear to be a fast moving material, however, it was very minor and the product was used without further purification.

Step 3: Cyclization Reaction

For the scale-up, ethoxyethanol was used as solvent in order to increase the temperature of the reaction to about 135° C. To 16.0 g (54 mmol) of the intermediate was dissolved in ~75 ml of ethoxyethanol. To this was added 10.2 g (2.0 eq.) of guanidine hydrochloride and 11.6 g (4.0 eq.) of NaOMe and the reaction was brought to a gentle reflux under argon. TLC was used to monitor the disappearance of starting material. After about 30 hours, the reaction was cooled and an additional 5.1 g (1.0 eq.) of guanidine hydrochloride and 2.9 g (1.0 eq.) NaOMe was added and the mixture brought back to reflux. By TLC, the reaction appeared complete after about 72 hours.

The reaction was allowed to cool and concentrated to about 20 ml on a rotary evaporator. The resulting slurry was diluted with about 600 ml of water and the pH was adjusted to 5-6 with con HOAc. The product precipitated out of the solution and was allowed to sit overnight at 0 degrees. The product was filtered and washed with copious amounts of water, followed by copious amounts of MeOH (remove any unreacted starting material) and air dried. Isolate ~13.5 g (~75%) of material. HPLC analysis showed that there was a minor polar impurity, the same one observed in the small scale reaction. The material can be used without further purification.

[2-(4-Amino-5-cyano-pyrimidin-2-ylamino)-ethyl]-carbamic acid tert-butyl ester (5 g, 18 mmol) was dissolved in 60 ml of a 50/50 v/v dichloromethane trifluoroacetic acid solution. Vigorous effervescence is observed upon addition of liquid to the solid. The solution is then stirred under an inert atmosphere for 30 minutes and then sample is taken for HPLC analysis to determine deprotection is complete. When deprotection is complete, the solution is concentrated to apparent dryness in vacuo.

In a separate container sodium metal (0.675 g) is added slowly to 30 ml of 2-methoxyethanol under an inert atmosphere until no sodium metal is observed in solution. Guanidine hydrochloride (2.645 g) solution in 2-methoxyethanol (30 ml) was made in a separate container. To this solution was added the sodium methoxyethoxide solution. Upon addition, a white precipitate of sodium chloride formed, and the resulting solution was stirred 30 minutes. This solution was filtered in an inert atmosphere, added to the crude residue from step one, and stirred vigorously. Within 15 minutes, a yellow precipitate was observed. The precipitate was filtered to yield N7-(2-Amino-ethyl)-pyrimido[4,5-d]pyrimidine-2,4,7-triamine (2.1 g, 52% yield).

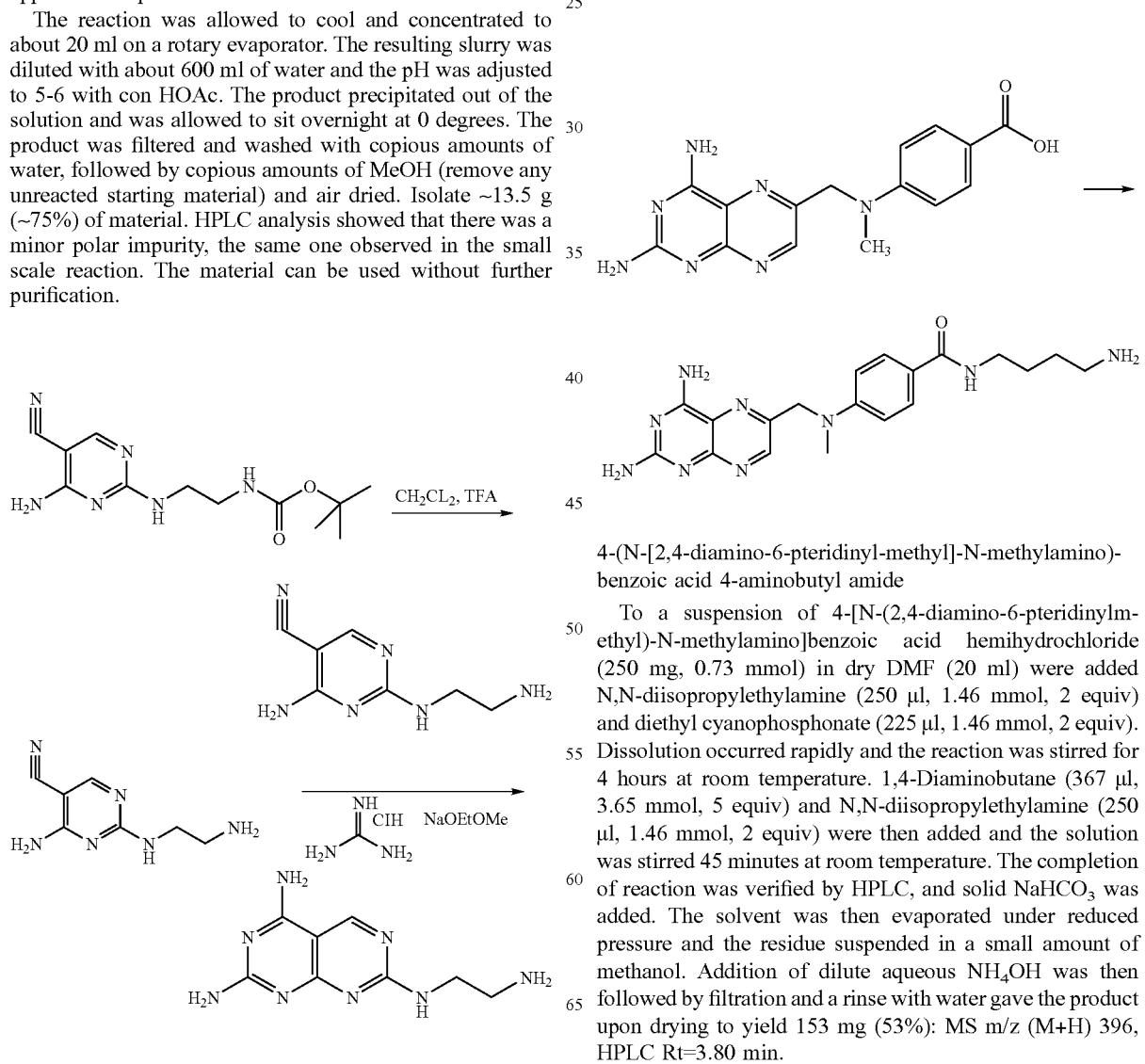

4-(N-[2,4-diamino-6-pteridinyl-methyl]-N-methylamino)-benzoic acid 4-aminobutyl amide To a suspension of 4-[N-(2,4-diamino-6-pteridinylmethyl)-N-methylamino]benzoic acid hemihydrochloride (250 mg, 0.73 mmol) in dry DMF (20 ml) were added N,N-diisopropylethylamine (250 µl, 1.46 mmol, 2 equiv) and diethyl cyanophosphonate (225 µl, 1.46 mmol, 2 equiv). Dissolution occurred rapidly and the reaction was stirred for 4 hours at room temperature. 1,4-Diaminobutane (367 µl, 3.65 mmol, 5 equiv) and N,N-diisopropylethylamine (250 µl, 1.46 mmol, 2 equiv) were then added and the solution was stirred 45 minutes at room temperature. The completion of reaction was verified by HPLC, and solid NaHCO$_3$ was added. The solvent was then evaporated under reduced pressure and the residue suspended in a small amount of methanol. Addition of dilute aqueous NH$_4$OH was then followed by filtration and a rinse with water gave the product upon drying to yield 153 mg (53%): MS m/z (M+H) 396, HPLC Rt=3.80 min.

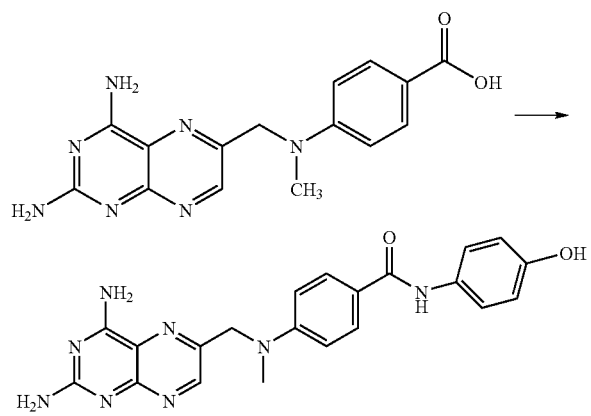

4-(N-[2,4-diamino-6-pteridinyl-methyl]-N-methylamino)-benzoic Acid 4-hydroxyphenyl amide To a suspension of 4-[N-(2,4-diamino-6-pteridinylmethyl)-N-methylamino]benzoic acid hemihydrochloride (100 mg, 0.29 mmol) in dry DMF (~6 ml) were added 2 equivalents of N,N-diisopropylethylamine (100 ul, 0.58 mmol) and 2 equivalents of diethyl cyanophosphonate (90 ul, 0.58 mmol). Dissolution occurred rapidly and the reaction was stirred for 3-4 hours at room temperature. For the 4-hydroxyphenyl amide, 1.05 equivalents of p-aminophenol (33 mg, 0.30 mmol) and 2 equivalents of N,N-diisopropylethylamine (100 ul, 0.58 mmol) were then added and the solution was stirred overnight at room temperature. The completion of reaction was verified by HPLC, and solid NaHCO$_3$ was added. The solvent was then evaporated under reduced pressure and the residue suspended in a small amount of methanol. Addition of dilute aqueous NH$_4$OH was then followed by filtration and a rinse with either dilute aqueous acetic acid gave the product upon drying. Yield 77 mg (0.19 mmol, 64%), MS m/z (M−H) 415, HPLC retention time 4.66 minutes.

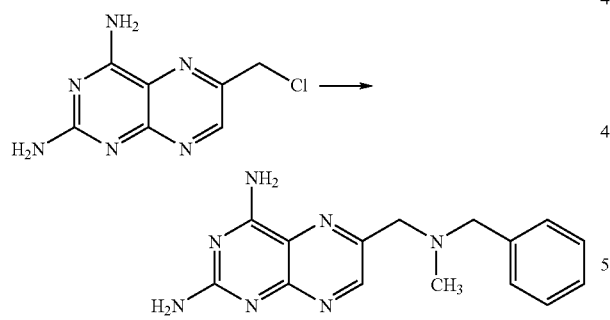

(N-benzyl[2,4-diamino-6-pteridinyl-methyl]-N-methylamine)

Five fold excess of N-methylbenzylamine (245.4 mg, 261 µl, 2.02 mmol) was dissolved in DMF (4 ml) in a 15 ml screw cap vial equipped with a magnetic stirrer. 2,4-Diamino-6-chloromethylpterin (100 mg, 0.405 mmol) was added and mixed well. The reaction mixture was stirred at 60° C. for 4 h. Analytical HPLC analysis of an aliquot confirmed the absence of pterin starting material. The solvent was removed under reduced pressure at 60° C. The resulting mixture was washed with EtOH (2×15 ml), then the solvent was removed under a stream of nitrogen and the resulting product dried on high vacuum 18 h. NMR and MS were obtained and confirm product structure and purity.

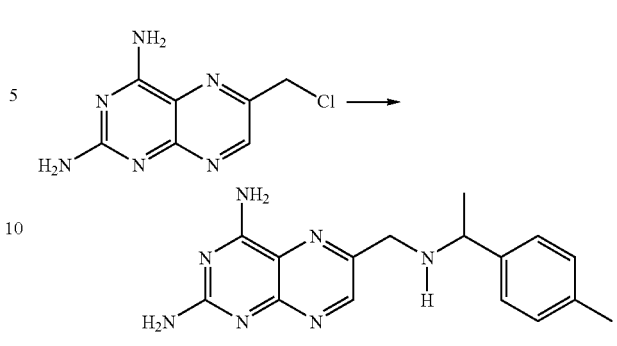

(N-(alpha-methyl-4-methylbenzy)[2,4-diamino-6-pteridinyl-methyl]-N-methylamine)

A five fold excess of (S)-(+)-alpha-4-dimethylbenzylamine (272 mg, 298 ul, 2.02 mmol) was dissolved in DMF (4 ml) in a 15 ml screw cap vial equipped with a magnetic stirrer. 2,4-Diamino-6-chloromethylpterin (100 mg, 0.405 mmol) was added and mixed well. The reaction mixture was stirred at 60° C. for 4 h. Analytical HPLC analysis of an aliquot confirmed the absence of pterin starting material. The solvent was removed under reduced pressure at 60° C. The resulting mixture was washed with EtOH (2×15 ml), then the solvent was removed under a stream of nitrogen and the resulting product dried on high vacuum 18 h. Analytical HPLC, 1H-NMR, and MS were consistent with the structure of the product and the product was of high purity.

Example 2

D-Ala-D-Ala-Ligase Ki Determination

The synthetic analogs of Example 1 were dissolved in dimethylsulfoxide (DMSO) at a concentration of 100 mM on the day of screening, using a vortex mixer and sonication if necessary for dissolution. The solutions were kept at room temperature until screening was completed.

A 10 mM NADH (Sigma) stock solution was prepared freshly on the day of screening by dissolving 32 µmol NADH in 3.2 ml double-distilled water. The NADH solution was kept on ice. Stock solutions containing 50 mM phosphoenolpyruvate (PEP; Sigma), 500 µM HERMES, 30 mM adenosine triphosphate (ATP; Sigma), 200 mM D-alanine (Sigma), and 4×core buffer (i.e., 400 mM Hepes, 40 mM magnesium chloride, and 40 mM potassium chloride), were also stored on ice. A stock solution of pyruvate kinase/lactate dehydrogenase (PK/LDH) was also obtained from Sigma.

Table of Final concentrations are dependent on the type of screening:

| Type of screening | ANALOGS' Ki Final concentration in enzyme mix | ANALOGS' % INHIBITION Final concentration in enzyme mix | ANALOGS' Ki AND MODE OF INHIBITION Final concentration in enzyme mix |
|---|---|---|---|
| Core buffer 4× | 1× | 1× | 1× |
| NADH 10 mM | 500 µM | 500 µM | 500 µM |
| PEP 50 mM | 2 mM | 2 mM | 2 mM |

| | ANALOGS' Ki Final concentration in enzyme mix | ANALOGS' % INHIBITION Final concentration in enzyme mix | ANALOGS' Ki AND MODE OF INHIBITION Final concentration in enzyme mix |
|---|---|---|---|
| Type of screening | | | |
| PK/LDH mix | 0.02 ml/ml enzyme stock solution | 0.02 ml/ml enzyme stock solution | 0.02 ml/ml enzyme stock solution |
| Hermes 500 µM | 200 nM | 400-600 nM | 200 nM |

| | ANALOGS' Ki Final concentration in substrate mix | ANALOGS' % INHIBITION Final concentration in substrate mix | ANALOGS' Ki AND MODE OF INHIBITION Final concentration in substrate mix | | |
|---|---|---|---|---|---|
| Type of screening | | | | | |
| Solution | A | Screening | A | B | C |
| ATP 30 mM | 4 mM | 20 uM | 4 mM | 4 mM | 100 uM |
| D-Ala 200 mM | 2 mM | 64 mM | 2 mM | 64 mM | 64 mM |
| Core buffer 1× | 1× | 1× | 1× | 1× | 1× |

Example 3

Determination of Ki of Analogs

For each set of test compounds, two 96-well plates were used: an inhibitor plate and an enzyme plate. The test compounds correspond to rows A-G of the plates. Adenosine (Sigma) dissolved in DMSO, used as a control, corresponds to row H of each plate.

The enzyme solution was allowed to equilibrate to 25° C.

Dilutions were prepared in the inhibitor plate as follows: 50 µl DMSO was added to each well of columns 1-11, rows A-G, of the inhibitor plate. 50 µl DMSO were added to each well of columns 1-11, row H. 100 µl of the 100 mM test solutions were added to column 12, rows A-G (i.e., the first compound in row A, the second compound in row B, and so on). 100 µl of a 100 mM Adenosine solution was added to column 12, row H.

50 µl of the test solution was transferred from column 12 in each row to column 11 of the same row, mixing the solution with the DMSO. 50 µl of solution was then transferred from column 11 in each row to column 10 in the same row, 50 µl from column 10 was transferred to column 9, and so on, down to column 2. No solution was transferred to column 1. Multichannel pipettors were used in making the serial dilution.

120 µl of the enzyme solution was added to each well of the enzyme plate.

The substrate solutions were brought to 25° C.

The analogs and enzymes were then incubated at 25° C. Since the reactions were initiated in columns, the analog addition is also in columns. At t=0 minutes, 5 µl analog was transferred from each well of columns 1-4 of the inhibitor plate to the corresponding well of the enzyme plate. At t=4 minutes, 5 µl analog was transferred from each well of columns 5-8 of the inhibitor plate to the corresponding well of the enzyme plate. At t=8 minutes, 5 µl analog was transferred from each well of columns 9-12 of the inhibitor plate to the corresponding well of the enzyme plate. The inhibitor plate was then frozen.

At t=18-19 minutes, the substrate solution was taken from 25° C. to a Spectromaxt UV-vis spectrophotometer. At t=20 minutes, within a 30 second timeframe, 125 µl of substrate solution was added to each well of columns 1-4, and the absorbance at 340 nm was read. At t=24 minutes and t=28 minutes, respectively, the process was repeated for columns 5-8 and 9-12.

Thus, the concentrations of the compounds in columns 1-12 in each row were 0, 1.9 µM, 3.9 µM, 7.8 µM, 15.6 µM, 31.2 µM, 62.5 µM, 125 µM, 250 µM, 500 µM, 1 mM, and 2 mM, respectively.

The reduction values were multiplied by −4.06 to convert mOD/min units to nM/sec (OD=λLM; λ=6220 1/Mcm; L=0.66 cm; mOD/sec=6220×0.66×(mM/sec)×60; (mOD/sec)×4.06=nM/sec); multiplied by −1 since NADH absorbance decreases as more product is generated).

Plots of reaction rates vs. inhibitor concentration were generated using Kaleidograph®, and $K_i$ values were determined after the data was fitted to the proper equation.

Most of the stages are alternatively done using the Sci-Clone automated liquid handling machine. These stages are: adding the enzyme mix to the enzyme plate, dispensing 50 ul DMSO in each well of colums 1-11 rows A-H of the inhibitor plate, serial dilutions of the analogs+adenosine control in the inhibitor plate, adding the analog inhibitors from the inhibitor plate to the enzyme plate, adding the substrate to the enzyme plate.

Example 4

Analogs % Inhibition

The assay procedure described above was repeated, except that inhibitor plates were prepared with 5 mM solutions of the inhibitors in the plates (rather than by serial dilutions), to result in a final concentration of 100 µM inhibitor in the final reaction mix. Enzyme activity in the presence of DMSO was used as a 100% activity reference.

Refer to the table above for exact concentrations.

Example 5

Analogs' Ki and Mode of Inhibition

The assay procedure described above was repeated, using three different substrate solutions, each in a different enzyme plate. The final concentrations in the reaction mixtures were: (A) 2 mM ATP and 1 mM D-alanine; (B) 2 mM ATP and 32 mM D-alanine; and (C) 50 µM ATP and 32 mM D-alanine. The same inhibitor plate was used with all three enzyme plates. Adenosine (Sigma) and cycloserine (Sigma) were used as controls. Refer to the table above for exact concentrations.

Example 6

Microdilution Antimicrobial Susceptibility Test Assay

Stock solutions of test compounds were prepared in DMF at a concentration of 5 mg/ml. Working solutions of the tested compounds were then prepared from the stock solutions, in Mueller-Hinton broth (MHB) with starting concentration of 64 µg/ml (i.e., 25.6 µl of stock solution in 974.4 µl of MHB=128 µg/ml, which was diluted with an equal volume of bacterial inoculum in the procedure that follows).

Bacterial inocula were prepared from overnight culture (i.e., one fresh colony from agar plate in 5 ml MHB; *H. influenzae* was grown in MHB with the addition of yeast extract, haematin, and NAD), centrifuged 2×5 min/3000 rpm (for *S. pneumoniae* and *H. influenzae*, 2×10 min/3000 rpm), and dispensed in 5 ml of fresh MHB each time, such that the bacterial suspension is diluted to obtain 100 colony forming units (cfu) in a microplate well (100 µl total volume).

The microplate wells were then filled with twofold dilutions of tested compound (50 µl), starting with 64 µg/ml. Columns 2-12 were filled with 50 µl of bacterial inoculum (final volume: 100 µl/well). The plates were incubated at 37° C. for 18-24 hours (*S. pneumoniae* was grown in a $CO_2$-enriched atmosphere).

The optical density of each well at 590 nm ($OD_{590}$) was then measured with a TECAN SpectroFluor Plush®, and minimum inhibitory concentration (MIC) was defined as the concentration that showed 90% inhibition of growth.

Example 7

MIC Determination Using Overexpressing *E. coli*

The procedure of Example 5 was repeated, with the following modifications:

The media used for growing bacteria was luria broth (LB) with added antibiotics (20 mg/l chloramphenicol for pBAD vectors, 100 mg/l ampicillin for pTAC vectors for plasmid selection) or M9 minimal media with D-mannitol as a carbon source.

The bacteria used for innoculum in LB were prepared as follows: Overnight culture was diluted 1:50 in a fresh LB media and incubated at 37° C. on a shaker at 250 rpm. After mid-log stage was reached ($OD_{600}$=0.5-1.0, about 3 hours), operon regulator (glucose, arabinose, or IPTG) was added, and the bacteria were further incubated for 3 hours. After 3 hours, $OD_{600}$ was measured again to estimate the bacterial count number, and the culture was diluted in LB media (antibiotics—chloramphenicol or ampicillin and regulators were added in double concentrations). Final bacterial inoculum was around 10,000 cfu/well.

The bacteria used for innoculum in M9 minimal media were prepared as follows: Overnight culture in LB was centrifuged 2×5 min/3000 rpm, washed with M9 media, diluted 1:50 in M9 minimal media, left at 37° C. for 14 hours ($OD_{600}$~0.5), operon regulator was added, and the bacteria were further incubated for 3 hours. After 3 hours, $OD_{600}$ was measured to estimate bacteria number, and the culture was diluted in M9 minimal media (antibiotics—chloramphenicol or ampicillin and regulators were added in double concentrations). The final bacterial innoculum was around 10,000 cfu/well.

Optical density was read out after 24 and 48 hours because of the slower bacterial growth in minimal media.

Example 8

Computer Modeling Protocol Used to Predict the Ligase Inhibitory Activity of Representative Analogs A virtual library of 7-substituted pteridines was generated by combining the chloromethylpteridine core shown below at left with a set of commercially available amines, according to the following scheme:

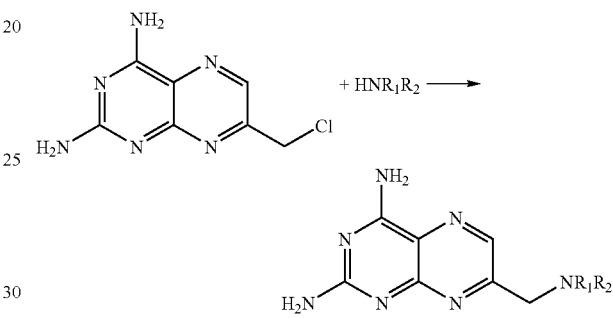

A set of 1500 commercially available amines was selected from Available Chemicals Directory (ACD, MDL) based on the following criteria:
MW<300;
No reactive or toxic functional groups;
General drug-like properties;
Available from known and reliable suppliers.

The corresponding pteridine derivatives were generated with the analog builder module implemented in Cerius2 (MSI). Conformational search was performed on the generated analogs with Catalyst (MSI), and a total of 32,000 conformers (~20 per molecule) were docked into the active site of D-Ala-D-Ala-ligase with the EUDOC program (Mayo Clinic). The conformation of the active site used for docking was derived from the x-ray crystallographic structure of the complex between the enzyme, ADP and a phosphinate inhibitor (obtained from the protein databank, pdb code: 2dln), with rearrangement and minimization of the side chain conformation of lysine 215.

The "best"—binding conformer of each molecule was then extracted from the docking results. The corresponding orientations in the active site were re-scored with a set of scoring functions implemented in the program CSCORE (Tripos). The solutions were then ranked on the basis of consensus scoring, using the function Chemscore as secondary criterion. A set of 76 high-ranking compounds were selected and re-docked with the FlexX program (Tripos), using the same conformation of the enzyme active site. The docking solutions were re-scored with CS CORE. The final selection of 50 compounds was based on consensus between the results obtained with the two docking programs. The predicted Ki's, calculated with Chemscore on the FlexX-generated solutions, were in the range 0.1-10 µM.

The calculations were performed on an SGI Octane (2×250 MHz CPU, 512 MB RAM), an SGI O2 (270 MHz CPU, 128 MB RAM) and a cluster of ten SGI Indigo2 computers (195 MHz CPU, 512 MB RAM).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound of the formula:

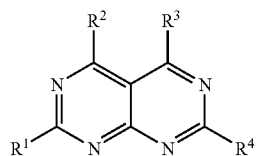

wherein
$R^1$ is $NH_2$;
$R^2$ is $NH_2$;
$R^3$ is selected from hydrogen, alkyl, amino, hydroxy, alkoxy, and alkylamino; and
$R^4$ is

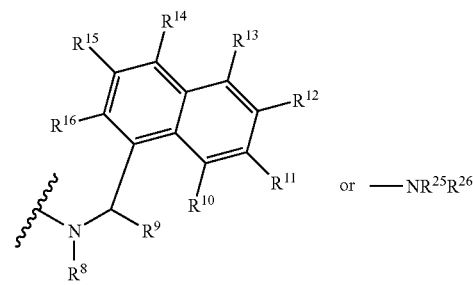

wherein
$R^8$ is selected from:
(i) hydrogen;
(ii) a substituted or unsubstituted, linear or branched alkyl group, wherein said group is optionally substituted with a substituent selected from amino, hydroxyl, aminoalkoxyl, guanindinyl, and carbonyl substituted with hydroxy;
provided that when $R^8$ is alkyl, said alkyl is optionally substituted with one or more substituents selected from hydroxyl, amino, carboxyl, piperidinyl, and pyrolidinyl;
(iii) unsubstituted hydroxycarbonylethyl or hydroxycarbonylethyl substituted with hydroxyl;
(iv) —$(CH_2)_n NH_2$, wherein n is 1, 2, 3, or 4; and
(v) —$(CH_2)_n C(=O)R^{17}$, wherein n is 1, 2, 3, or 4; and $R^{17}$ is selected from $NH_2$,

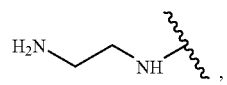

-continued

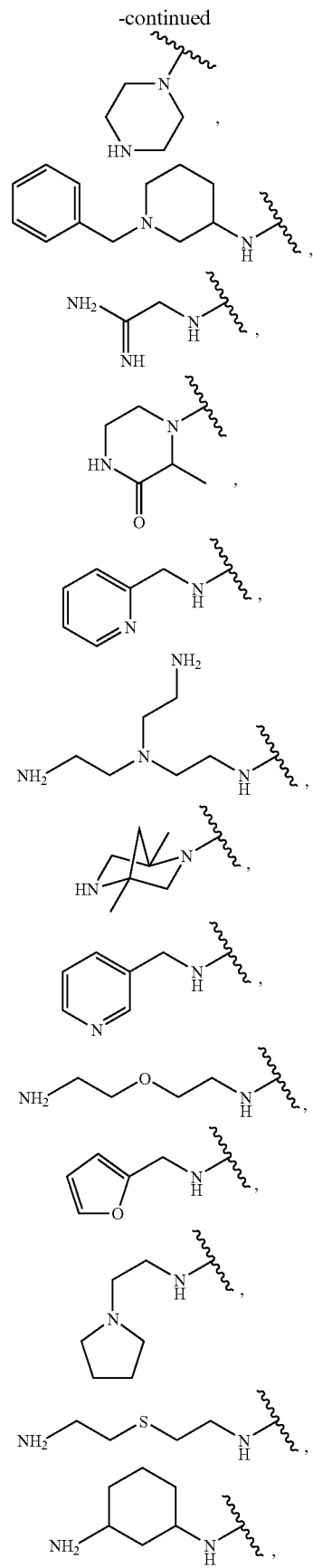

-continued

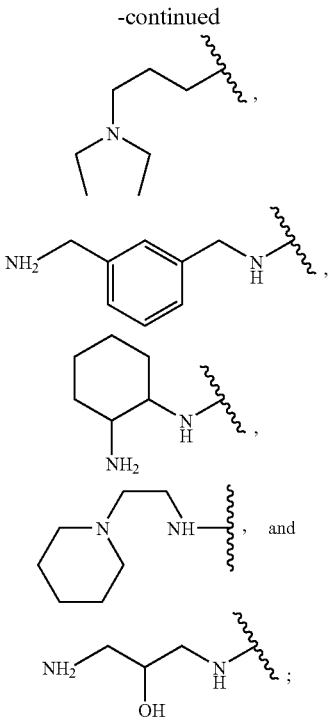

$R^9$ is selected from hydrogen, cyclopropyl, trifluoromethyl, unsubstituted C1-C2 alkyl, and methyl substituted with cyclopropyl, hydroxyl, and amino;

$R^{10}$, $R^{11}$, $R^{12}$, $R^{15}$ and $R^{16}$ are independently selected from hydrogen, alkoxy, halogen, and alkyl;

$R^{13}$ and $R^{14}$ are independently selected from hydrogen, alkoxy, halogen, and alkyl, or $R^{13}$ and $R^{14}$ are joined together to form an alkylene group;

$R^{25}$ is selected from hydrogen, alkyl, hydroxyalkyl, and aralkyl; and $R^{26}$ is selected from haloalkyl, hydroxyl, tetrahydronaphthyl, —CH(CH$_3$)C(=O)NH(naphthyl)quinolinylmethyl, benzothiophenylmethyl, —CH$_2$CH$_2$NHC(=O)(aryl), and —C(H)(aryl)(R$^{29}$), wherein aryl is optionally substituted with one or more halogen groups, and wherein the aryl group in —C(H)(aryl)(R$^{29}$) is a naphthyl or benzothiophenyl group; and $R^{29}$ is hydrogen.

2. The compound of claim 1, wherein $R^4$ is:

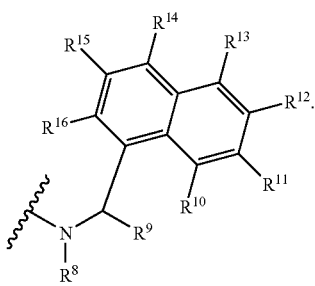

3. The compound of claim 2, wherein $R^9$ is hydrogen or methyl.

4. The compound of claim 3, wherein
$R^8$ is —(CH$_2$)$_n$C(=O)R$^{17}$, wherein $R^{17}$ is NH$_2$; and
$R^9$ is hydrogen.

5. The compound of claim 2, wherein $R^8$ is —(CH$_2$)$_n$NH$_2$.

6. A compound of the formula:

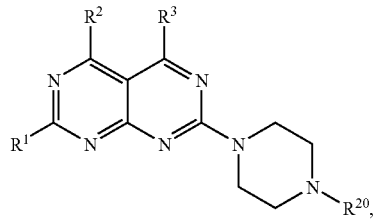

wherein
$R^1$ is NH$_2$;
$R^2$ is NH$_2$;
$R^3$ is selected from hydrogen, alkyl, amino, hydroxy, alkoxy, and alkylamino; and
$R^{20}$ is hydrogen.

7. The compound of claim 1, wherein $R^4$ is

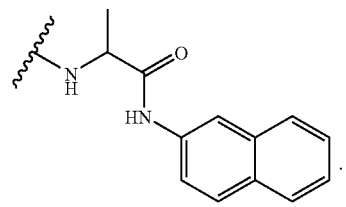

8. An antibacterial composition comprising a therapeutically effective amount of a compound of claim 1 and an excipient suitable for administration to a subject.

9. A method of making a compound of claim 1, comprising
reacting a substituted guanidine of the formula

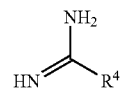

with an $R^3$-substituted alkoxylmethylenemalonitrile of the formula

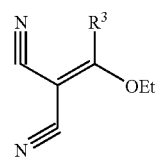

to form a cyanoaminopyrimidine; and
condensing the cyanoaminopyrimidine with guanidine to form a pyrimidopyrimidine of claim 1.

10. The method of claim 9, wherein the substituted guanidine contains a substituent selected from —Cl, —Br, and —S-lower alkyl.

11. A method of inhibiting D-Ala-D-Ala ligase, comprising exposing D-Ala-D-Ala ligase to a compound of formula II

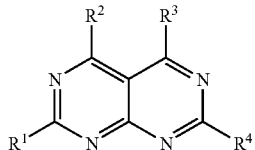

wherein $R^1$ is $NH_2$;

$R^2$ is $NH_2$;

$R^3$ is selected from hydrogen, alkyl, amino, hydroxy, alkoxy, and alkylamino; and $R^4$ is

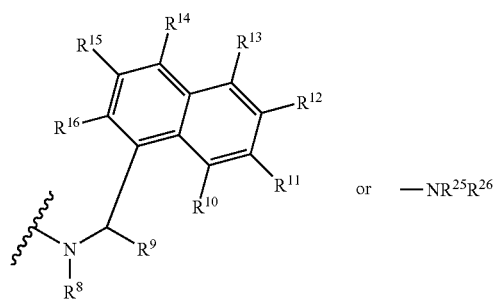 or —$NR^{25}R^{26}$ wherein $R^8$ is selected from:

(i) hydrogen (ii) a substituted or unsubstituted, linear or branched alkyl group, wherein said group is optionally substituted with a substituent selected from amino, hydroxyl, aminoalkoxyl, guanindinyl, and carbonyl substituted with hydroxy;

provided that when $R^8$ is alkyl, said alkyl is optionally substituted with one or more substituents selected from hydroxyl, amino, carboxyl, piperidinyl, pyrolidinyl;

(iii) unsubstituted hydroxycarbonylethyl or hydroxycarbonylethyl substituted with hydroxyl;

(iv) —$(CH_2)_n NH^2$, wherein n is 1, 2, 3, or 4; and (v) —$(CH_2)_n C(=O)R^{17}$, wherein n is 1, 2, 3, or 4; and $R^{17}$ is selected from $NH_2$,

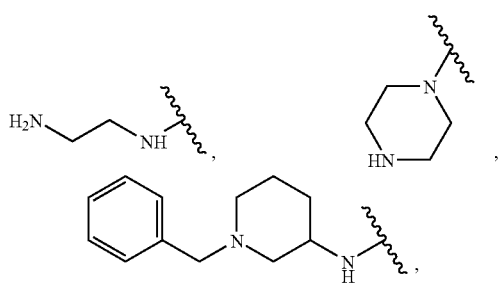

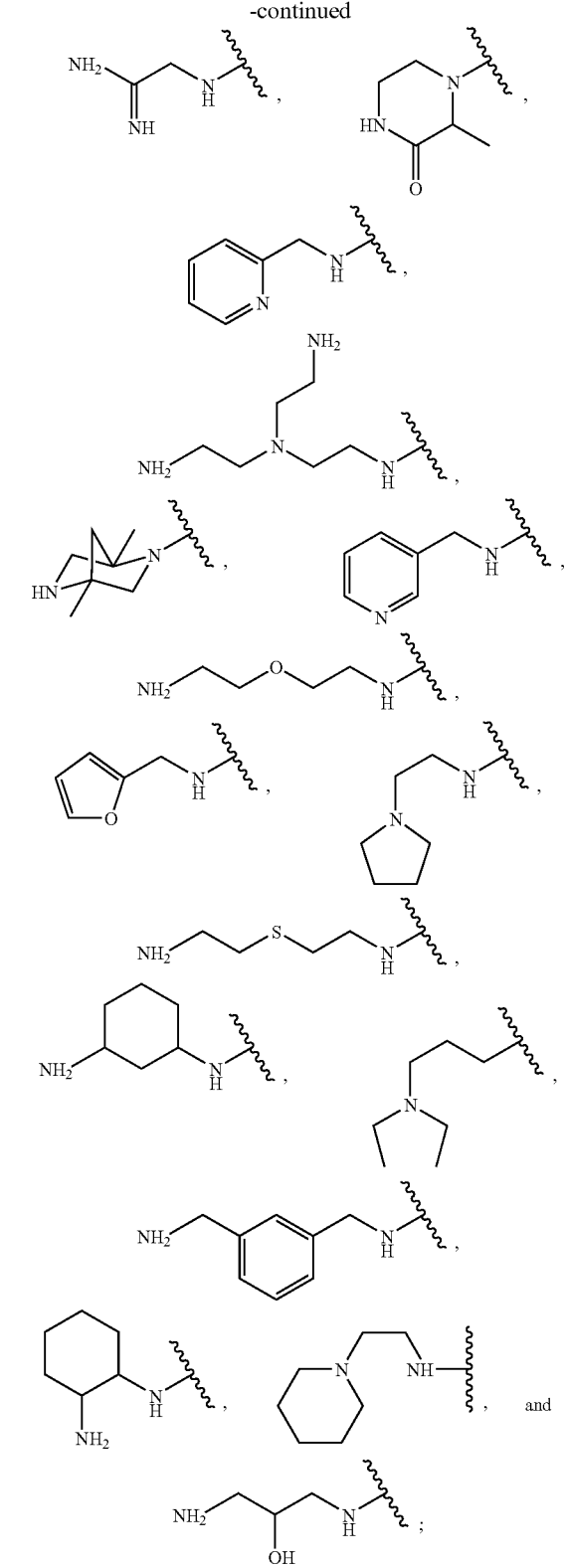

$R^9$ is selected from hydrogen, cyclopropyl, trifluoromethyl, unsubstituted C1-C2 alkyl, and methyl substituted with cyclopropyl, hydroxyl, or amino;

$R^{10}$, $R^{11}$, $R^{12}$, $R^{15}$, and $R^{16}$ are independently selected from hydrogen, alkoxy, halogen, and alkyl, and R¹³ and R¹⁴ are independently selected from hydrogen, alkoxy, halogen, and alkyl, or R¹³ and R¹⁴ are joined together to form an alkylene group;

R²⁵ is selected from hydrogen, alkyl, hydroxyalkyl, and aralkyl; and

R²⁶ is selected from haloalkyl, hydroxyl, tetrahydronaphthyl, —CH(CH₃)C(═O)NH(naphthyl), quinolinylmethyl, benzothiophenylmethyl, —CH₂CH₂NHC(═O)(aryl), and —C(H)(aryl)(R²⁹), wherein aryl is optionally substituted with one or more halogen groups, and wherein the aryl group in —C(H)(aryl)(R²⁹) is a naphthyl or benzothiophenyl group; and R²⁹ is hydrogen.

12. The method of claim 11, wherein R³ is hydrogen.

13. The method of claim 11, wherein the D-Ala-D-Ala ligase comprises a sequence at least 90% identical to the sequence of a D-Ala-D-Ala ligase from a species selected from *Escherichia coli, Chlamydia pneumoniae, Chlamydia trachomatis, Yersinia pestis, Haemophilus influenzae, Haemophilus ducreyi, Pseudomonas aeruginosa, Pseudomonas putida, Xylella fastidiosa, Bordetella pertussis, Thiobacillus ferrooxidans, Neisseria meningitidis, Neisseria gonorrhoeae, Buchnera aphidicola, Bacillus halodurans, Geobacter sulfurreducens, Rickettsia prowazekii, Zymomonas mobilis, Aquifex aeolicus thermophile, Thermotoga maritima, Clostridium difficile, Enterococcus faecium, Streptomyces toyocaensis, Amycolatopsis orientalis, Enterococcus gallinarum, Enterococcus hirae, Enterococcus faecium, Enterococcus faecalis, Streptococcus pneumoniae, Streptococcus pyogenes, Staphylococcus aureus, Bacillus subtilis, Bacillus stearothermophilus, Deinococcus radiodurans, Synechocystis sp., Salmonella typhimurium, Mycobacterium tuberculosis, Mycobacterium avium, Mycobacterium smegmatis, Legionella pneumophila, Leuconostoc mesenteroides, Borrelia burgdorferi, Treponema pallidum, Vibrio cholerae,* and *Helicobacter pylori.*

14. A method of treating a bacterial infection, comprising administering to a subject in need thereof an effective amount of a compound of formula II:

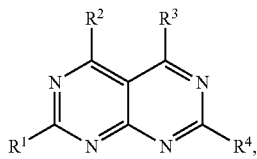

wherein
R¹ is NH₂;
R² is NH₂
R³ is selected from hydrogen, alkyl, amino, hydroxy, alkoxy, and alkylamino; and R⁴ is

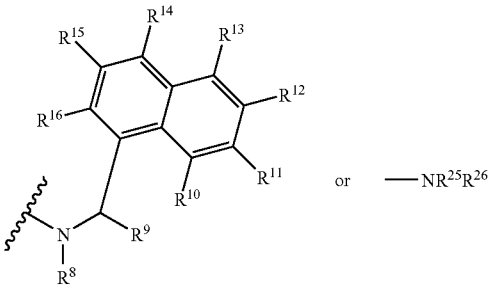

wherein
R⁸ is selected from:
(i) hydrogen
(ii) a substituted or unsubstituted, linear or branched alkyl group, wherein said group is optionally substituted with a substituent selected from amino, hydroxyl, aminoalkoxyl, guanindinyl, and carbonyl substituted with hydroxy;
provided that when R⁸ is alkyl, said alkyl is optionally substituted with one or more substituents selected from hydroxyl, amino, carboxyl, piperidinyl, pyrolidinyl;
(iii) unsubstituted hydroxycarbonylethyl or hydroxycarbonylethyl substituted with hydroxyl;
(iv) —(CH₂)ₙNH₂, wherein n is 1, 2, 3, or 4; and
(v) —(CH₂)ₙC(═O)R¹⁷, wherein n is 1, 2, 3, or 4; and R¹⁷ is selected from NH₂,

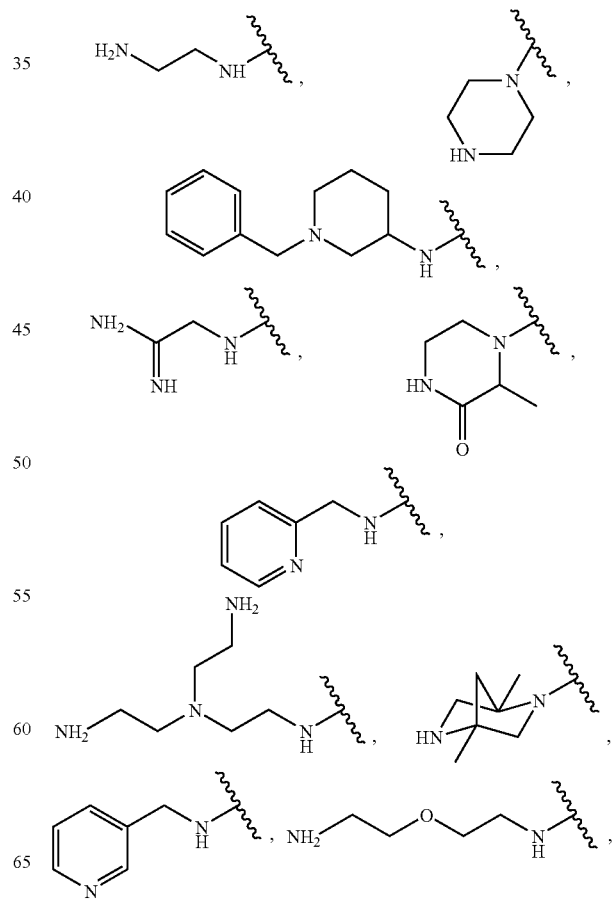

-continued

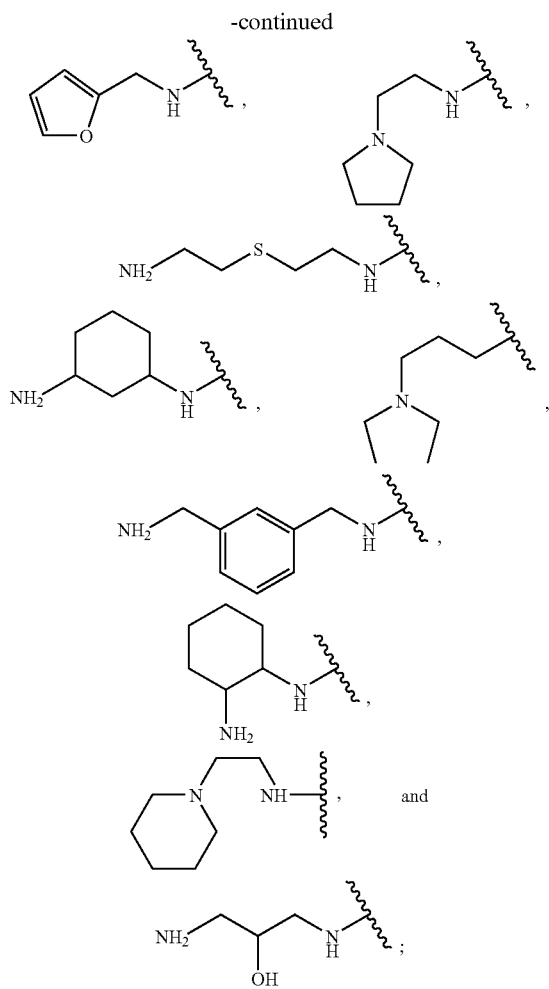

R⁹ is selected from hydrogen, cyclopropyl, trifluoromethyl, unsubstituted C1-C2 alkyl, and methyl substituted with cyclopropyl, hydroxyl, or amino;

$R^{10}$, $R^{11}$, $R^{12}$, $R^{15}$, and $R^{16}$ are independently selected from hydrogen, alkoxy, halogen, and alkyl, and $R^{13}$ and $R^{14}$ are independently selected from hydrogen, alkoxy, halogen, and alkyl, or $R^{13}$ and $R^{14}$ are joined together to form an alkylene group;

$R^{25}$ is selected from hydrogen, alkyl, hydroxyalkyl, and aralkyl; and $R^{26}$ is selected from haloalkyl, hydroxyl, tetrahydronaphthyl, —CH(CH₃)C(=O)NH(naphthyl), quinolinylmethyl, benzothiophenylmethyl, —CH₂CH₂NHC(=O)(aryl), and —C(H)(aryl)(R²⁹), wherein aryl is optionally substituted with one or more halogen groups, and wherein the aryl group in —C(H)(aryl)(R²⁹) is a naphthyl or benzothiophenyl group; and R²⁹ is hydrogen.

15. The method of claim 14, wherein the subject is an animal.

16. The method of claim 14, wherein $R^3$ is hydrogen.

17. A method of inhibiting bacterial growth in a non-living system, comprising contacting the system with a compound of formula II

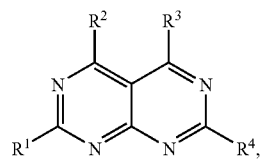

wherein
$R^1$ is NH₂;
$R^2$ is NH₂; and
$R^3$ is selected from hydrogen, alkyl, amino, hydroxy, alkoxy, and alkylamino; and
$R^4$ is

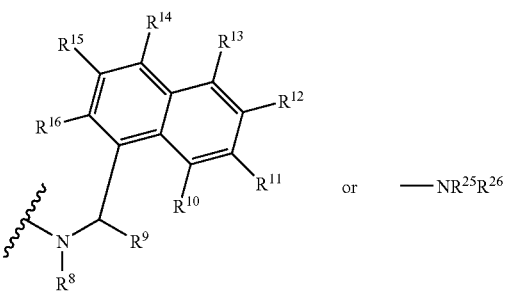  or  —NR²⁵R²⁶ wherein
$R^8$ is selected from:
(i) hydrogen
(ii) a substituted or unsubstituted, linear or branched alkyl group, wherein said group is optionally substituted with a substituent selected from amino, hydroxyl, aminoalkoxyl, guanindinyl, and carbonyl substituted with hydroxy;
provided that when $R^8$ is alkyl, said alkyl is optionally substituted with one or more substituents selected from hydroxyl, amino, carboxyl, piperidinyl, pyrolidinyl;
(iii) unsubstituted hydroxycarbonylethyl or hydroxycarbonylethyl substituted with hydroxyl;
(iv) —(CH₂)ₙNH₂, wherein n is 1, 2, 3, or 4; and
(v) —(CH₂)ₙC(=O)R¹⁷, wherein n is 1, 2, 3, or 4; and
$R^{17}$ is selected from NH₂,

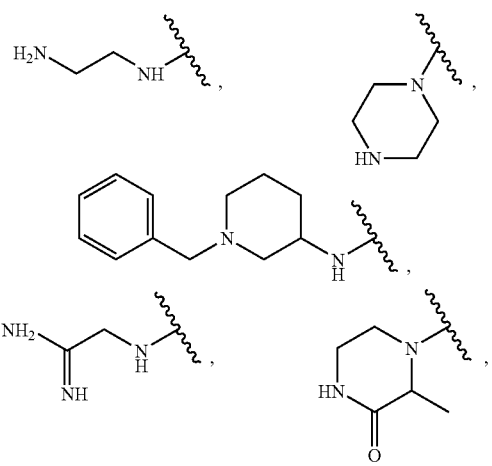

-continued

$R^9$ is selected from hydrogen, cyclopropyl, trifluoromethyl, unsubstituted C1-C2 alkyl, and methyl substituted with cyclopropyl, hydroxyl, or amino;

$R^{10}$, $R^{11}$, $R^{12}$, $R^{15}$, and $R^{16}$ are independently selected from hydrogen, alkoxy, halogen, and alkyl, and $R^{13}$ and $R^{14}$ are independently selected from hydrogen, alkoxy, halogen, and alkyl, or $R^{13}$ and $R^{14}$ are joined together to form an alkylene group;

$R^{25}$ is selected from hydrogen, alkyl, hydroxyalkyl, and aralkyl; and $R^{26}$ is selected from haloalkyl, hydroxyl, tetrahydronaphthyl, —CH(CH$_3$)C(=O)NH(naphthyl), quinolinylmethyl, benzothiophenylmethyl, —CH$_2$CH$_2$NHC(=O) (aryl), and —C(H)(aryl)(R$^{29}$), wherein aryl is optionally substituted with one or more halogen groups, and wherein the aryl group in —C(H)(aryl) (R$^{29}$) is a naphthyl or benzothiophenyl group; and R$^{29}$ is hydrogen;

wherein the amount of compound is effective to inhibit bacterial growth.

18. The method of claim 17, wherein $R^3$ is hydrogen.

19. A compound of the formula:

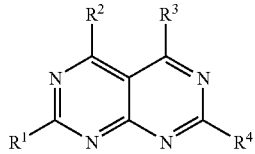

wherein
$R^1$ is NH$_2$; and
$R^2$ is NH$_2$;
$R^3$ is selected from the group consisting of hydrogen, alkyl, amino, hydroxy, alkoxy, and alkylamino; and
$R^4$ is selected from:

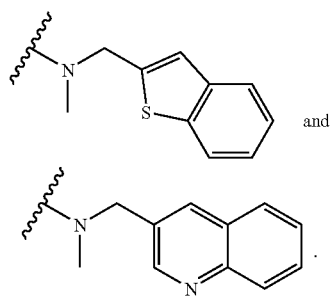

20. An antibacterial composition comprising a therapeutically effective amount of a compound of claim 19 and an excipient suitable for administration to a subject.

21. A method of making a compound of claim 19, comprising reacting a substituted guanidine having the formula

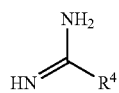

with an $R^3$-substituted alkoxylmethylenemalonitrile of the formula

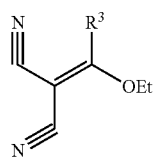

to form a cyanoaminopyrimidine; and
condensing the cyanoaminopyrimidine with guanidine to form a pyrimidopyrimidine of claim 20.

22. The compound of claim 3, wherein
$R^8$ is —$(CH_2)_nC(=O)R^{17}$, wherein $R^{17}$ is selected from:
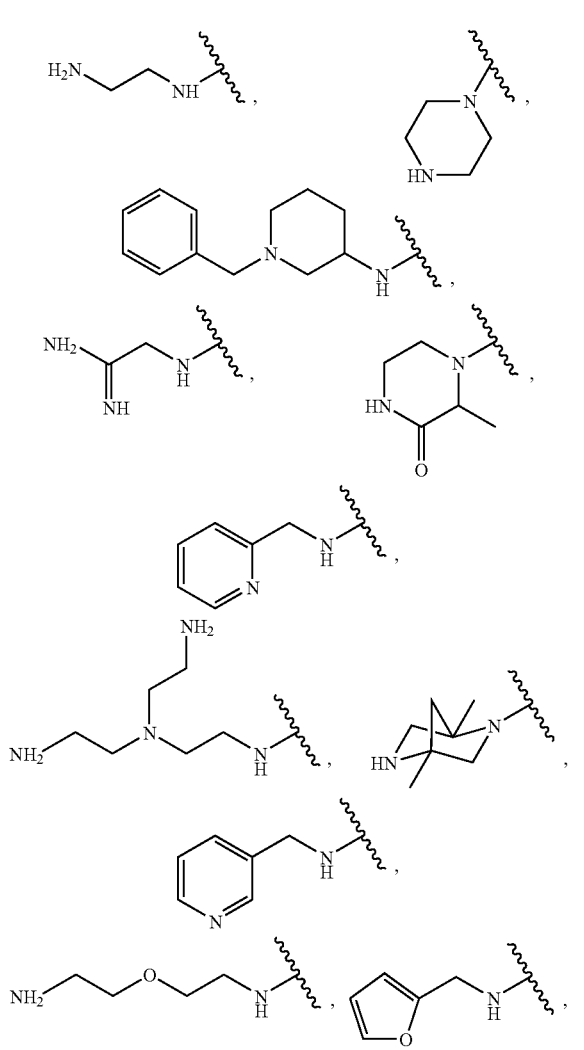
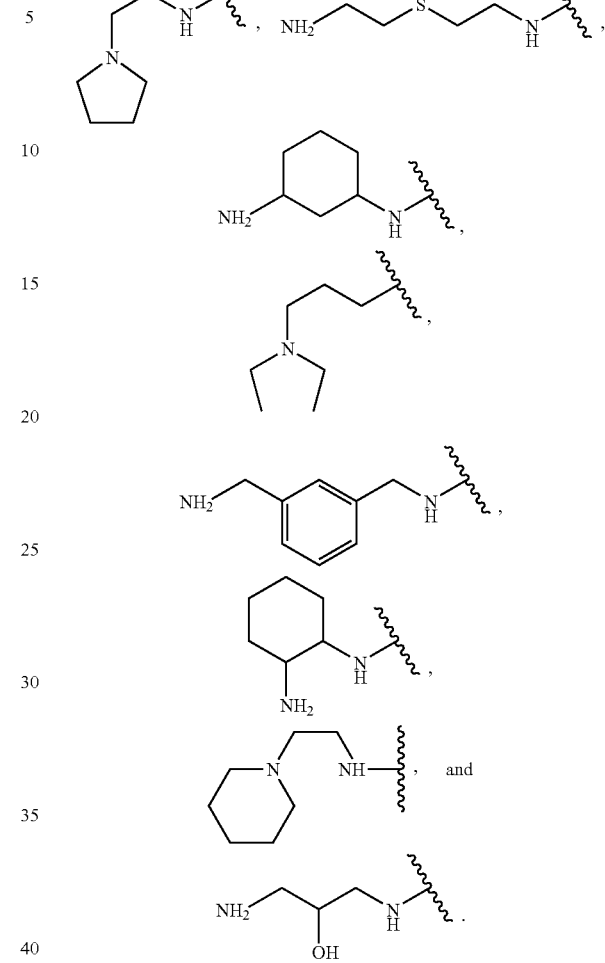
* * * * *